(12) United States Patent
Le Buannec et al.

(10) Patent No.: US 7,972,603 B2
(45) Date of Patent: Jul. 5, 2011

(54) STABLE IMMUNOGENIC PRODUCT COMPRISING ANTIGENIC HETEROCOMPLEXES

(75) Inventors: Helene Le Buannec, Paris (FR); Daniel Zagury, Paris (FR)

(73) Assignee: Neovacs, Paris (FR)

( * ) Notice: Subject to any disclaimer, the term of this patent is extended or adjusted under 35 U.S.C. 154(b) by 0 days.

(21) Appl. No.: 10/527,975

(22) PCT Filed: Sep. 16, 2003

(86) PCT No.: PCT/FR03/02733
§ 371 (c)(1),
(2), (4) Date: Mar. 15, 2005

(87) PCT Pub. No.: WO2004/024189
PCT Pub. Date: Mar. 25, 2004

(65) Prior Publication Data
US 2006/0067944 A1    Mar. 30, 2006

(30) Foreign Application Priority Data

Sep. 16, 2002   (FR) ...................................... 02 11455

(51) Int. Cl.
*A61K 39/21*   (2006.01)
*C07K 1/00*    (2006.01)
*C07K 14/00*   (2006.01)

(52) U.S. Cl. .................... 424/187.1; 424/188.1; 530/350

(58) Field of Classification Search .......................... None
See application file for complete search history.

(56) References Cited

U.S. PATENT DOCUMENTS

| | | | |
|---|---|---|---|
| 5,008,116 A | 4/1991 | Cahn | |
| 6,093,405 A * | 7/2000 | Zagury et al. | 424/198.1 |
| 6,340,461 B1 | 1/2002 | Terman | |
| 6,455,045 B1 * | 9/2002 | Zagury et al. | 424/184.1 |
| 6,878,370 B1 * | 4/2005 | Zagury et al. | 424/85.1 |
| 7,022,482 B2 * | 4/2006 | Zagury et al. | 435/6 |
| 2002/0098203 A1 | 7/2002 | Gustavsson et al. | |
| 2004/0028647 A1 * | 2/2004 | Zagury et al. | 424/85.1 |

FOREIGN PATENT DOCUMENTS

| | | |
|---|---|---|
| WO | WO 9101146 A1 | 2/1991 |
| WO | WO 9846642 A1 * | 10/1998 |
| WO | WO 9957981 A1 | 11/1999 |
| WO | WO 0211759 A1 * | 2/2002 |
| WO | WO 0222164 A1 | 3/2002 |

OTHER PUBLICATIONS

Tam, J Immunol Methods Sep. 13, 1996;196(1):17-32.*
Wedlock et al., Immunol and Cell Biology. 1999; 77:28-33.*
Antigen Design and Sera Purification, Sigma Genosys, 2006.*
Musselli et al., J Cancer Res Clin Oncol. Oct 2001: 127(Suppl 2):R20-R26).*

(Continued)

*Primary Examiner* — Cherie M Woodward
(74) *Attorney, Agent, or Firm* — Young & Thompson

(57) ABSTRACT

The invention relates to a stable immunogenic product for the induction of antibodies against one or more antigenic proteins in a subject. The invention is characterised in that it comprises proteinaceous immunogenic heterocomplexes which are formed by associations between (i) antigenic protein molecules and (ii) proteinaceous carrier molecules and in that less than 40% of the antigenic proteins (i) are linked to the proteinaceous carrier molecules (ii) by a covalent bond.

12 Claims, 12 Drawing Sheets

OTHER PUBLICATIONS

Shirakawa et al, "VEGF121-specific monoclonal antibodies, hybridomas producing them, and determination of VEGF using the antibodies," Chemical Abstracts Service, 1999, XP00224246.

Kim et al., "Comparison of the effect of different immunological adjuvants on the antibody and T-cell response to immunization with MUCI-KLH and GD3-KLH conjugate cancer vaccines," Vaccine 18, (2000), pp. 597-603, XP002242468.

* cited by examiner

STABLE IMMUNOGENIC PRODUCT COMPRISING ANTIGENIC HETEROCOMPLEXES

This is a nationalization PCT/FR03/002733 filed Sep. 16, 2003 and published in French.

FIELD OF THE INVENTION

The present invention relates to stable immunogenic products comprising immunogenic protein heterocomplexes for obtaining a humoral immune response with production of specific antibodies raised against one or more antigens, in particular against a <<self>> antigen, as well as their use in the field of vaccines.

PRIOR ART

Obtaining a high level antibody response from a given antibody, in an individual, is an object commonly sought, whether the antigen is a <<foreign>> antigen or a <<self>> antigen.

However, the problem of a good recognition of the antigen against which an antibody response is being sought, in an individual, should be solved in a number of cases, more particularly (a) when the antigen of interest behaves like a <<hapten>>, i.e. a low molecular mass chemical structure which is little or not immunogenic under a free form, but that, once fixed on a high molecular mass molecule, is able to induce the production of specific antibodies of such a hapten, and (b) when the antigen of interest is a self protein, i.e. a protein being naturally produced in the individual, for which there exists an immune tolerance due to the deletion of corresponding lymphocyte T clones, during the development of the immune system.

In order to cause, or increase, the recognition of an antigen of interest by B cells, various immunogenic constructions were developed in the state of the art.

A first immunogenic construction form comprises a covalent coupling of the antigen of interest on a carrier molecule, the carrier molecule bringing structures recognized by the auxiliary T lymphocytes (<<T helper>> cells), in association with class II molecules of the Histocompatibility Major Complex (HMC), and activating the auxiliary T lymphocytes then producing various cytokins, amongst which IL-2, said cytokins activating in turn the specific B cell clones of the antigen of interest. The specific B cells of the antigen of interest, once activated, multiply and produce antibodies specific to the antigen of interest, which is the objective being sought. Generally, such a type of immunogenic constructions comprises products of the covalent chemical coupling between the antigen of interest and the carrier molecule, which, after purification and removal steps of the non coupled products, are final products with a well defined chemical structure.

The first form of an immunogenic construction is for example illustrated by the article by Richard and al. describing the preparation of products of the covalent coupling between IL-9 and ovalbumin (Proc. Natl. Acad. Sci. USA, Vol. 97(2): 767-772). It is also illustrated in such U.S. Pat. No. 6,340,461 (Terman) which discloses coupling products between one or more copies of an antigen of interest, against which a specific antibody response is being sought in an individual, and a carrier molecule consisting in a <<Superantigen>>. The antigen of interest is coupled exclusively covalently to the carrier molecule, for example, by means of glutaraldehyde (also called <<pentanedial>>), the non covalently coupled products being removed in order to obtain a chemically well defined final product.

Optionally, the product from the covalent coupling between the antigen of interest and the superantigen could be prepared in the form of a polymer of said coupling product, for example, through a non covalent bond of the monomeric coupling products between one another, through ionic interactions, adsorption interactions as well as biospecific interactions. For example, the monomeric coupling products could form complexes with highly positively or negatively charged molecules, through salt bridges produced in low ionic strength conditions. Larges complexes of monomeric coupling products are prepared using charged polymers such as poly(L-glutamic acid) or poly(L-lysine) polymers. According to another embodiment of a monomeric coupling product polymer, the exclusively covalent coupling products between the antigen of interest and the superantigen could be adsorbed or coupled non covalently at the surface of microparticles, such as latex beads or other hydrophobic polymers.

A second embodiment of such immunogenic constructions commonly called <<MAP>> structure (for <<Multi-Antigenic Protein>>) generally have the form of a protein backbone comprised of a linear or branched, poly(lysine) polymer, onto which one or more antigens of interest are covalently bound.

A third embodiment of such immunogenic constructions consists in microparticles onto which fixed the antigen(s) of interest is/are bound. Various forms of antigen carrier microparticles are known.

Are known, for example, iscomes (for <<immunostimulating complexes>>) comprised of an antigenic complex and an adjuvant, the QuilA compound.

Liposomes are also known having the same inconvenients as the iscomes, i.e. more particularly some toxicity and immunological side effects, due to their lack of purity.

Biodegradable microparticles are also known such as lactic acid and glutamic acid polymers (Aguado and Lambert, 1992, Immuno. Biol., Vol. 184: 113-125) as well as starch particles (US Patent Application 2002/0098203—Gutaysson et al.), in the polymeric matrix of which antigens of interest are trapped. Such particles release the antigen under their soluble form during the degradation of the polymeric matrix.

Particles have also been disclosed exclusively comprised of hybrid recombinant proteins, as disclosed in French Patent Application FR 2,635, 532 (Thiollais et al.).

Porous microspheres are also known wherein the antigens are immobilized within micropores through captation or physical coupling, as disclosed in the U.S. Pat. No. 5,008,116 (Cahn).

However, the various solutions suggested in the state of the art share in common at least one technical inconvenient related to their preparation method, i.e. the loss of a high proportion of the antigenic material of interest, due to a necessary step for removing the non coupled or non adsorbed antigens.

Moreover, while the prior art techniques allow to provide an association between the low molecular mass antigen of interest with a carrier molecule, they are generally not adapted to coupling a high molecular mass antigen of interest, for example, of more than 10 kDa, with the carrier molecule, because, in particular, of steric hindrances preventing coupling a high number of molecules of antigens of interest having a high molecular mass with an identical carrier molecule.

Finally, most if not all the known peptide antigenic constructions encompass in their structure a single carrier molecule, which is technically inconvenient when the objective is to induce a preventive or therapeutic immune response both against the antigen of interest and the carrier molecule itself.

There is therefore a need in the state of the art for improved immunogenic constructions allowing for the production of a high level of antibodies specific to an antigen of interest in an individual where such a humoral immune response is sought, less expensive, simple to prepare and able to be synthetized reproducibly.

SUMMARY OF THE INVENTION

The present invention provides new immunogenic constructions allowing to solve the various technical problems encountered with the immunogenic constructions as known in the prior art and allowing to meet the above-described various technical needs.

The object of the invention is to provide a stable immunogenic product for inducing antibodies raised against one or more antigenic proteins in a subject, characterized in that it comprises protein immunogenic heterocomplexes consisting of associations between (i) antigenic protein molecules and (ii) carrier protein molecules and in that less than 40% of the antigenic proteins (i) are covalently linked to carrier protein molecules (ii).

Another object of the invention is also an immunogenic product comprising stable protein immunogenic heterocomplexes for inducing antibodies raised against one or more antigenic proteins in a subject, each heterocomplex comprising (i) a plurality of antigenic proteins, linked to a (ii) carrier protein molecule, characterized in that less than 40% of the antigenic proteins (i) are covalently linked to carrier protein molecules (ii).

Preferably, the immunogenic heterocomplex making up the immunogenic product according to the invention comprises 5 to 50 antigenic proteins (i) for one carrier protein molecule (ii), preferably 20 to 40 antigenic proteins (i) for one carrier protein molecule (ii).

Preferably, the covalent bonds between one or more antigenic proteins (i) and the carrier protein molecules (ii) occur by means of a functional binding chemical agent.

It is meant under antigenic molecule of interest, any protein comprising one or more B epitopes of a native antigenic protein against which the production of antibodies is being sought. Said antigenic molecule of interest can consist in the native protein itself or a protein derivate of the native protein, such as a peptide fragment of the native protein, as well as any biologically inactivated form of the native protein obtained through chemical, physical treatment or genetic mutation. The antigenic molecule of interest could also consist in a homo-oligomer or a homo-polymer of the native protein as well as a homo-oligomer or a homo-polymer of a peptide fragment of the native protein. The antigenic protein of interest could also consist in a hetero-oligomer or a hetero-polymer comprising a combination of several distinct peptide fragments initially included in the native protein.

According to the general embodiment of an immunogenic product according to the invention, the carrier protein molecule (ii) is an immunogenic protein inducing the production of T helper lymphocytes and/or of cytotoxic T lymphocytes raised against cells having at their surface said carrier protein molecule or any peptide being derived therefrom, in association with presenting molecules of the Major Histocompatibility Complex (MHC), respectively of class I and/or class II. The carrier protein molecule (ii) could also be an immunogenic protein inducing both the production of T helper lymphocytes and the production of antibodies by B lymphocytes raised against the carrier protein.

According to an embodiment of particular interest, the immunogenic product is characterized in that the carrier protein molecule (ii) is an immunogenic protein inducing the production of T cytotoxic lymphocytes raised against cells having at their surface said carrier protein molecule or any peptide being derived therefrom, in association with molecules of the Major Histocompatibility Complex (MHC) class I.

The preferred immunogenic products according to the invention are selected amongst immunogenic products comprising the following heterocomplexes, wherein the antigenic proteins (i), on the one hand, and the protein carrier molecule (ii), on the other hand, are respectively:

a) (i) IL-4 and (ii) KLH;
b) (i) alpha interferon and (ii) KLH;
c) (i) VEGF and (ii) KLH;
d (i) IL-10 and (ii) KLH;
e) (i) alpha interferon and (ii) gp 160 of VIH1
f) (i) IL-4 and (ii) the Bet v 1 allergenic antigen; and
g) (i) VEGF and (ii) the papillomavirus E7 protein;
h) (i)) the inactivated VIH1 Tat protein and (ii) the VIH1 gp120 protein.
i) (i) an IgE isotype human antibody and (ii) the inactivated VIH1 Tat protein;
j) (i) the ricin β fragment and (ii) KLH.

The invention also relates to a composition, more particularly, a pharmaceutical composition, an immunogenic composition or a vaccine composition, characterized in that it comprises an immunogenic product such as hereinabove described.

It also relates to a method for preparing an immunogenic product according to any one of claims 1 to 16, characterized in that it comprises the following steps of:

a) incubating the antigenic proteins (i) and the carrier molecule (ii) in a molar ratio (i):(ii) ranging from 10:1 to 50:1 in the presence of a binding chemical; and b) collecting the immunogenic product comprising immunogenic heterocomplexes being prepared in step a).

DESCRIPTION OF THE FIGURES

FIG. 5A relates to mice immunized with murine VEGF. FIG. 5B relates to mice immunized with the immunogenic product comprising KLK-VEGF heterocomplexes. FIG. 5C illustrates control mice injected with Freund's Incomplete Adjuvant (FIA).

DETAILED DESCRIPTION OF THE INVENTION

Figure 1:
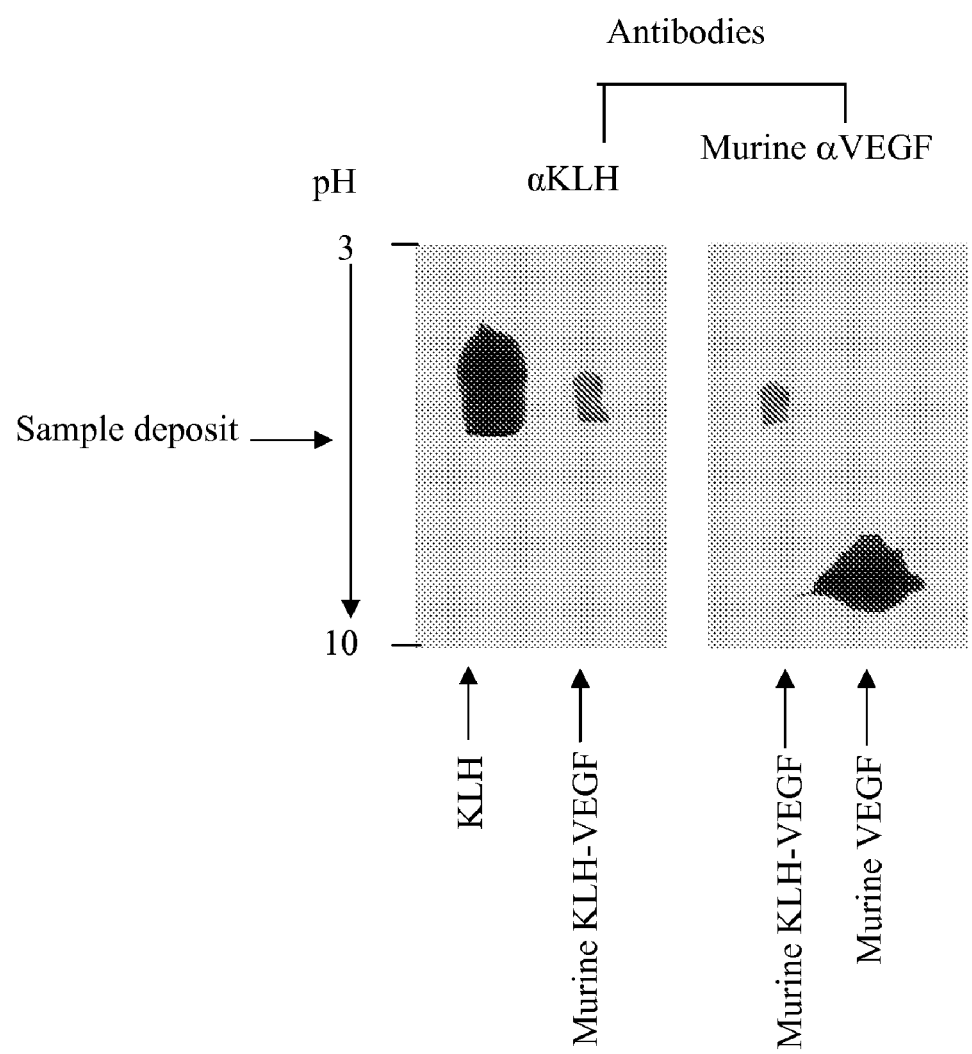
FIG. 1 illustrates the characterization of the immunogenic product comprising murine KLH-VEGF heterocomplexes through isoelectrofocusing in an agarose gel followed by the emergence of proteins through immuno-blotting (<<Western Blot>>).

The invention provides new immunogenic constructions inducing a high level of production of antibodies specific to an antigen of interest, in an individual.
The Immunogenic Protein Heterocomplexes According to the Invention It has been shown according to the invention that the production of a high level of antibodies specific to an antigen of interest could be obtained, in an individual, through the immunization of such an individual with an immunogenic product where said antigen of interest is associated with a carrier protein molecule, the association between said antigen of interest and said carrier protein being partially covalent and partially non covalent.

More specifically, it has been shown according to the invention that an excellent antibody response raised against an antigen of interest is obtained when an individual is being immunized with a stable immunogenic product comprising protein heterocomplexes, wherein the heterocomplexes comprise stable associations between antigen of interest and said carrier protein molecule and wherein only a low proportion of such associations is due to a covalent bond between the antigen of interest and the carrier protein molecule, the other associations between the antigen of interest and the carrier protein molecule being produced by weak bonds, ionic interactions, hydrogen bonds, Van der Waals forces, etc.

In particular, it has been shown according to the invention that an optimum antibody response is reached when, in a stable immunogenic product such as described hereinabove, less than 40% of the molecules of the antigen of interest are covalently linked to the carrier protein molecules. According to the invention, an antigenic molecule of interest is covalently linked to a carrier protein molecule by <<one>> covalent bond means that said molecule of antigen of interest is covalently linked, chemically, to said carrier protein molecule, by at least one covalent bond, i.e. optionally by two covalent bonds or more.

The percentage of carrier protein molecules and of antigenic protein proteins of interest linked between one another through covalent bonds in an immunogenic product of the invention can be easily checked by the man of the art.

For example, determining the percentage of antigenic molecules of interest linked to the carrier protein molecules through a covalent link in an immunogenic product of the invention could be made using the following steps of:

(i) submitting said immunogenic product in solution to denaturing and reducing conditions;

(ii) performing a size exclusion chromatography step with the product as obtained at the end of step (ii) during which the various protein components with decreasing molecular mass are successively eluted from the size exclusion chromatography support;

(iii) measuring the amount of antigen of interest linked through a covalent bond to the carrier molecule in the eluate fraction containing the protein components with the highest molecular mass;

(iv) comparing the amount of antigen of interest measured in step (iii) with the total amount of antigen of interest initially included in the starting immunogenic product.

In step (i) of the method for determining the above-described covalent link percentage, incubating a given amount (in number of moles or in weight) of the immunogenic product of the invention under denaturing and reducing conditions leads to a disassociation of the weak bonds between the various protein components not linked between one another through a covalent bond.

Amongst preferred denaturing conditions there is the presence of urea, for example, in the final 8M concentration, or the presence of SDS, for example, in the 1% final concentration in total weight of the solution containing the immunogenic product. Amongst preferred reducing conditions there is the presence of β-mercaptoethanol, for example in the 5% final concentration of the total volume of the solution containing the immunogenic product.

In step (ii) of the method for determining the percentage of molecules of antigen of interest and molecule of carrier protein linked between one another through covalent bonds, the size exclusion chromatography support is selected by the man of the art according to his technical general knowledge. For example, the man of the art could make use of chromatographic supports as marketed by the Pharmacia Corporation under the <<Superdex 75™>> and <<Superdex 200™>> trade marks.

In step (ii), the molecular fraction corresponding to the carrier molecule covalently linked to the molecules of antigen of interest is eluted first, before the eluate fraction(s) containing the antigen of interest under a free form. The antigen of interest being eluted under a free form corresponds to the fraction of the antigen of interest, which was not covalently linked to the carrier molecule, within the starting immunogenic product. It is on the high molecular mass protein fraction that occurs the measurement of the amount of the antigen of interest covalently linked to the carrier protein molecule, for example, in an immuno-enzyme test, in a radioimmunologic test or in an immunofluorescence test, either direct or indirect (<<sandwich>>), using antibodies specific to the antigen of interest and which do not have any immunologic reaction crossed with the carrier protein molecule.

In step (iii), the amount of the antigen of interest covalently linked with the carrier protein molecule, being measured as described hereinabove, is compared with the initial amount of the antigen of interest being included in the given amount (in number of moles or in weight) of the starting immunogenic product and the percentage of the antigen of interest is thereby calculated, which is covalently linked to the carrier protein molecule, in the immunogenic product of the invention.

The percentage of carrier protein molecules and of antigenic protein proteins of interest linked between one another through covalent bonds, in an immunogenic product of the invention, can be easily checked by the man of the art, making use of a second method comprising the following steps of:

a) immobilizing on a support of specifically antibodies raised against the carrier protein;

b) brinding into contact the antibodies raised against the carrier protein, which were immobilized on the support in step a), with a known amount of molecules of the immunogenic product to be tested comprising said carrier protein and an antigenic protein of interest;

c) removing the molecules of the immunogenic product which are not linked to the anti-carrier protein antibodies immobilized in step a), by means of a buffering aqueous solution comprising one or more protein denaturing agents;

d) d1) bringing into contact (i) immunogenic complexes formed in step c) between the immobilized anti-carrier protein antibodies and the molecules of the immunogenic product with (ii) antibodies specifically raised against the carrier protein;

d2) separately from step d1), bringing into contact the immunogenic complexes formed in step c) between the immobilized anti-carrying protein antibodies and the molecules of the immunogenic product with (ii) antibodies specifically raised against the antigenic protein of interest;

e) e1) quantifying the antibodies added in step d1) having been linked to the carrier protein;

e2) quantifying the antibodies added in step d2) having been linked to the antigenic protein;

f) calculating the ratio between:
(i) the amount of anti-carrier protein bound antibodies measured in step e1); and
(ii) the amount of anti-carrier protein bound antibodies measured in step e2), said ratio consisting in the proportion of carrier protein molecules and antigenic protein molecules of interest being linked between one another through covalent bonds, within the starting immunogenic product.

In step c) of the above described method, the use of an aqueous washing solution containing one or more protein denaturing agents leads to a denaturation of the immunogenic product linked to the anti-carrier protein antibodies, resulting in the release, in the washing solution, of antigenic protein molecules of interest which are not covalently linked to the carrier protein molecules. Therefore, in step d2) of the method, only the antigenic protein molecules of interest being covalently linked to the carrier protein molecules are quantified.

Preferably, the denaturing buffering solution used in step c) contains a surfactant such as TWEEN®20, in a final concentration of 0.1% v/v.

in steps d1) and d2), the amounts of bound antibodies are preferably measured through incubating antigen-antibodies complexes formed at the end of each of said steps with a new antibody being labelled through a detectable molecule, respectively:

(i) in step d1), a new antibody directed against an the anti-carrier protein antibody and labelled with a detectable molecule;

(ii) in step d2), a new antibody directed against an antibody anti-antigen protein of interest and labelled with a detectable molecule.

The detectable molecule is indiscriminately either a radioactive molecule, a fluorescent molecule or an enzyme. As an enzyme, peroxydase could more particularly be used, its presence being revealed through colorimetry, after incubation with the ortho-phenylenediamine (OPD) substrate.

A detailed protocol of the above-mentioned method is described in the examples.

By way of illustration, it has been shown according to the invention, using the first or the second above described quantification methods that:

in the immunogenic product comprising heterocomplexes between the KLH carrier molecule and human alpha interferon molecules, from 3 to 8% of the alpha interferon molecules are covalently linked to the KLH carrier protein molecule;

in the immunogenic product comprising the heterocomplexes between the KLH carrier protein molecule and murine IL-4 molecules, about 11% of the IL-4 molecules are covalently linked to the KLH carrier protein molecule.

Obviously, depending on the preparations, the percentage of molecules of antigenic protein of interest covalently linked to the carrier protein molecules could significantly vary. However, in all cases, such a percentage is always lower than 40%.

The object of the invention is to provide a stable immunogenic product for inducing antibodies raised against one or more antigenic proteins in a subject, characterized in that it comprises protein immunogenic heterocomplexes comprising associations between (i) antigenic protein molecules and (ii) carrier protein molecules and in that less than 40% of the antigenic proteins (i) are covalently linked to carrier protein molecules (ii).

Another object of the invention is also to provide an immunogenic product comprising stable protein immunogenic heterocomplexes for inducing antibodies raised against one or more antigenic proteins in a subject, each heterocomplex comprising (i) a plurality of antigenic proteins, linked to a (ii) carrier protein molecule, characterized in that less than 40% of the antigenic proteins (i) are covalently linked to carrier protein molecules (ii).

Most preferably, the antibodies with their production being induced by the immunogenic product of the invention comprise <<neutralizing>> or <<blocking>> antibodies. A <<neutralizing>> or a <<blocking>> antibody is defined, according to the invention, as an antibody the binding of which on the native protein blocks the biological activity of such a native protein, which is an important objective being sought by the invention, when the native protein against which the antibodies are raised has a deleterious biological activity for the organism, within the targeted pathological context of an individual to be treated, for example, when the native protein has an angiogenic activity, an immunosuppressive activity, as well as an allergenic activity, more particularly an interleukin-4 production inducing activity.

A <<carrier protein molecule>>, included in the immunogenic product of the invention, means any protein or peptide being at least 15 amino acids long, whatever its amino acid sequence, and which, when partially covalently being associated to the molecules of the antigen of interest for forming protein heterocomplexes making up the immunogenic product of the invention, allows for a large number of molecules of the antigen of interest to be presented to the B lymphocytes.

According to a first aspect, the carrier protein molecule consists in one protein or one peptide being at least 15 amino acid long, or also an oligomer of such a peptide, comprising one or more auxiliary T epitopes ("helper") able to activate auxiliary T lymphocytes ("T helper") of the host organism for producing cytokins, including interleukin 2, such cytokins, in turn, activating and inducing the proliferation of B lymphocytes, which, after maturation, will produce antibodies raised against the antigenic protein (i).

According to a second aspect, a carrier protein molecule consists in one protein or one peptide being at least 15 amino acid long, or also an oligomer of such a peptide, comprising besides one or more auxiliary T epitopes ("helper"), as described in the above-mentioned first aspect, one or more cytotoxic T epitopes, able to induce a cell immune response through the production of cytotoxic T lymphocytes specific of the carrier protein molecule, such lymphocytes being able to specifically recognize cells expressing on their surface said carrier protein or any peptide being derived therefrom, in association with class 1 Histocompatibility Major Complex (HMC) molecules. If need be, the carrier protein molecule consists in one oligomer of one protein or one peptide, further comprising besides one or more T helper epitopes, one or more above defined cytotoxic T epitopes.

According to a third aspect, a carrier protein molecule consists in one protein or one peptide being at least 15 amino acid long, as well as one oligomer of such a peptide, comprising besides one or more auxiliary T epitopes ("helper") as defined in the first aspect, one or more B epitopes, able to induce the production of antibodies by lymphocytes raised against the carrier protein.

In some embodiments, the carrier protein, besides its T helper, used for activating an antibody response against the antigen of interest, could also activate a cytotoxic response against cells carrier peptides of the carrier and/or stimulate an antibody response against such a carrier protein molecule.

The carrier protein molecule could also consist in a homo-oligomer or a homo-polymer of the native protein, from which it is derived, as well as a hetero-oligomer or a homo-polymer of a peptide fragment of the native protein, from which it is derived. The antigenic protein of interest could also consist in a hetero-oligomer or a hetero-polymer comprising a combination of several distinct peptide fragments initially included in the native protein from which it is derived.

As used herein, the expression <<antigenic protein>> means any protein or any peptide being at least 10 amino acid long, including a hapten peptide, able to be specifically recognized by receptors for the antigens expressed by the B lymphocytes of a host organism, whether human or animal, more particularly a mammal, such antigenic protein, once included in an immunogenic product of the invention, stimulating the production of antibodies recognizing said antigenic protein.

It is meant under <<antigenic protein>> any protein comprising one or more B epitopes of the native antigenic protein against which the production of antibodies if being sought. Said antigenic molecule of interest could consist in the native protein itself or a protein derivate of the native protein, such as a peptide fragment of the native protein, as well as any biologically inactivated form of the native protein obtained through chemical, physical treatment or genetic mutation.

The antigenic molecule of interest could also consist in a homo-oligomer or a homo-polymer of the native protein as well as a homo-oligomer or a homo-polymer of a peptide fragment of the native protein. The antigenic protein of interest could also consist in a hetero-oligomer or a hetero-polymer comprising a combination of several distinct peptide fragments initially included in the native protein.

In an immunogenic product according to the invention, advantageously, less than 30% and preferably less than 20% of antigenic proteins (i) are covalently linked to the carrier protein molecules (ii).

In an immunogenic product according to the invention, advantageously, at least 1%, and preferably at least 2%, of the antigenic proteins (i) are covalently linked to the carrier molecules (ii).

It has been shown that an immunogenic product according to the invention, such as hereinabove defined, is stable in an aqueous solution. The stability of an immunogenic product of the invention is more particularly characterized in that said immunogenic product has its own isoelectric point, distinct from the isoelectric point of at least one of its protein components, respectively the antigenic protein (i) and the carrier protein molecule (ii), and in that it therefore migrates according to a distinct protein strip from at least one of its protein strips respectively corresponding to both protein components making it up in isoelectrofocusing trials.

It has also been shown, through immunoblotting trials (<<Western blot>>), that the immunogenic product of the invention migrates in an electrophorese gel, under non denaturating conditions, according to a single protein strip, which illustrates the fact that said immunogenic product has the form of a homogeneous population of soluble protein constructions.

Moreover, it has been shown that the antigenic protein (i) as well as the protein molecule (ii) included under the form of protein heterocomplexes in the immunogenic product of the invention were both recognized by antibodies specifically recognizing each of such proteins. Thus, the immunogenic product according to the invention comprises the antigenic protein (i) and the carrier protein molecule (ii) in their native structure. Such a technical feature of the immunogenic product according to the invention is particularly advantageous for inducing an immune response against native antigens, i.e. an efficient and truly protective immune response of the host organism. It has been more particularly shown that an immunogenic product according to the invention induces, in the host organism to which it is administered, the induction of a strong efficient humoral response against native antigens, associated to the production of neutralizing or blocking antibodies, towards the deleterious biological activity of such native antigens.

It has been shown according to the invention, with various antigens of interest, that the humoral immune response obtained using an immunogenic product such as defined hereinabove, was 10 to 1000 times higher than the humoral immune response obtained with the administration of a conventional covalent conjugate between the antigen of interest and the carrier protein molecule.

Preferably, in an immunogenic heterocomplex included in the immunogenic product of the invention, the plurality of antigenic proteins (i) is made up of a plurality of specimens of a single antigenic protein.

Thus, according to a most preferred embodiment, the immunogenic product of the invention is implemented for obtaining specific antibodies raised against a single antigen of interest.

It has also been shown according to the invention that an immunogenic product comprising immunogenic heterocomplexes such as hereinabove defined, is particularly well adapted to the immunization of an individual, through the production of antibodies, against a <<self antigen>> of interest, i.e. against a protein being naturally produced by said individual, for which there exists a tolerance of the immune system, in particular an at least partial deletion of auxiliary lymphocyte T clones (T helper cells) specifically recognizing said antigen.

In other words, the presentation of the <<self>> antigen to the cells of said individual's immune system, under the form of an immunogenic product comprising immunogenic heterocomplexes of the invention, allows to <<break>> the tolerance of the individual's immune system towards such an antigen. Without wishing to be bound to any theory, the Applicant believes that the opportunity to obtain a high level of antibody response against a <<self>> antibody is due to the presence within the heterocomplex of numerous epitopes of the <<auxiliary T>> type (or T helper) carried by the carrier protein molecule, activating the auxiliary T lymphocytes, and the various cytokins produced by the activated auxiliary T lymphocytes, including IL-2, allows to promote some activation of the B cells to <<self>> antigens present in the latent state within the organism, and to thereby break the immune tolerance of B cells to <<self>> antigens.

Thus, according to a preferred embodiment, the immunogenic product of the invention is characterized in that the antigenic proteins (i) consists in a plurality of specimens of a protein being normally recognized as a self protein by the cells of said subject's immune system.

As the major proportion, more than 60%, of associations between the antigen of interest and the carrier protein molecule, occurs through non covalent interactions, there exists no other theoretical limitation in the number of molecules of the antigen of interest associated with a single carrier protein molecule, than the steric availability of the molecules of the antigen of interest to such a carrier molecule. In particular, the number of molecules of the antigen of interest associated to a single carrier protein molecule is not limited by the number of chemically reactive functions carried by the carrier molecule allowing for creating covalent links with a plurality of molecules of the antigen of interest. Consequently, the only physical limitation seems to be the number of sites of the carrier protein molecule (ii) available to the antigenic protein (i).

For the same reasons, the size of the antigen of interest to be associated to the carrier protein molecule is not either strictly limited, the antigen of interest consequently being able to consist in full proteins of at least 10 kDa, such as the various cytokines, as IL-4, IL-10, VEGF as well as the alpha interferon.

Moreover, even for the antigens of interest consisting in full proteins with a molecular mass higher than 10 kDa, an immunogenic heterocomplex of the invention can comprise an association of several antigens of interest on a single carrier molecule, if the size of the carrier molecule makes it possible.

When the carrier protein molecule has a small size, for example a size lower than 10 kDa, or even lower than 5 kDa, the Applicant believes, without wishing to be bound to any theory, that the partially covalent associations between the antigen of interest and said carrier protein, forming the protein heterocomplexes included in the immunogenic product of the invention, allow for such a conformation of heterocomplexes that both the antigen of interest and the carrier protein molecule are available to receptors of the immune system cells.

This is even an additional technical advantage provided to the immunogenic product comprising heterocomplexes such as hereinabove defined, as the presentation to B lymphocytes of a plurality of specimens on one single carrier molecule, included in the heterocomplex, enhances the <<capping>> phenomenon through <<cross-linking>> of receptors of the B cell recognizing the antigen, contributing to the activation of the B cell receiving, in addition, activation signals coming from cytokins produced by the activated auxiliary T lymphocytes activated by means of auxiliary T epitopes carried by carrier protein molecule.

Thus, according to a most preferred embodiment of the immunogenic product, the latter comprises 5 to 50 antigenic proteins (i) for one carrier protein molecule (ii), preferably 20 to 40 antigenic proteins (i) for one carrier protein molecule (ii).

The number of molecules of the antigen of interest on one single carrier protein molecule respectively depends on the size of the carrier molecule and on the size of the molecule of the antigen of interest. The bigger the carrier molecule is and offers a large association surface with the antigen of interest, the more the immunogenic heterocomplex will comprise, for one single of the carrier molecules it contains, a higher number of specimens of the molecule of the antigen of interest. Similarly, the more reduced the size of the molecule of the antigen of interest is, the larger the number of specimens will be of the molecule of the antigen of interest on the same carrier molecule.

By way of illustration, it has been shown according to the invention that when the carrier protein molecule is KLH, 20 to 40 molecules of IL-4, IL-10, alpha interferon or VEGF are associated to each carrier molecule.

It has been shown that the solubility of the immunogenic product in an aqueous solution varies with the modification of the balances mastering the molecular interactions within heterocomplexes, more particularly the electrochemical balances depending on the so-called <<weak>> (non covalent) links as well as the respective concentrations in antigenic proteins and the carrier protein molecule, as well as with the conditions of ionic strength, pH and temperature.

Preferably, the covalent bonds between one or more antigenic proteins (i) and the carrier protein molecule (ii) occur by means of a bifunctional bonding chemical agent.

Such a chemical agent could be cyanogen bromide, glutaraldehyde, carbodiimide or succinic anhydride.

As for carbodimides, the following compounds could be used: 1-cyclohexyl-3-(2-morpholinyl-(4-ethyl)carbodiimide (CMC), 1-ethyl-3-(3-dimethyaminopropyl)carbodiimide (EDC) and 1-ethyl-3-(4-azonia-4,4-limethylpentyl)carbodiimide, 1-cyclohexyl-3-(2-morpholinyl-(4-ethyl)-carbodiimide, (1-ethyl-3-(3-dimethyaminopropyl carbodiimide (EDC) and 1-ethyl-3-(4-azonia-4,4-dimethylpentyl)carbodiimide.

As homo-bifunctional coupling agents, the following compounds could be used:
  N-hydroxysuccinimide, dithiobis(succinimidylpropionate) esters, disuccinimidyl suberate, and disuccinimidyl tartrate; bifunctional imidoesters dimethyl adipimidate, dimethyl pimelimidate, and dimethyl suberimidate;
  reagents with a sulphydryl, 1,4-di-[3'-(2'-pyridyledithio)propionamido]butane, bismaleimidohexane, and bis-N-maleimido-1,8-octane;
  bifunctional halides of the aryl type and 4,4'-difluoro-3,3'-dinitrophenylsulfone;

SMCC (succinimidyl-4-(N-maleimidomethyl)cyclohexane-1-carboxylate);
STAB (N-succinimidyl(4-iodoacetyl)aminobenzoate);
SMPB (succinimidyl-4-(p-maleimidophenyl)butyrate);
GMBS (N-(.gamma.-maleimidobutyryloxy)succinimide ester);
MPBH (4-(4-N-maleimidophenyl)hydrazide butyric acid);
M2C2H (4-(N-maleimidomethyl)cyclohexane-1-carboxyl-hydrazide);
SMPT (succinimidyloxycarbonyl-alpha-methyl-alpha-(2-pyridyl-dithio)toluene); and
SPDP (N-succinimidyl 3-(2-pyridyldithio)propionate).

Preferably, the bonding chemical agent to be used comprises at least two reactive aldehyde functions.

Most preferably, the bonding chemical agent is glutaraldehyde.

After the product comprising protein heterocomplexes has been formed through a coupling of carrier protein molecules with antigenic proteins with the use of the bonding chemical agent, the resulting product could be stabilized by means of a protein stabilizing agent, such as formaldehyde, able to create intrachain bonds.

The immunogenic products comprising immunogenic heterocomplexes of the invention have the form of microparticles soluble in solution, in particular in an aqueous solution, their average size varying depending on (i) the size of the carrier protein molecule, (ii) the size and the number of antigenic proteins associated to one single carrier protein molecule and (iii) the number of carrier molecules associated to the antigenic proteins present in a heterocomplex particle.

It has been found that the heterocomplex microparticles described in the examples have an average size ranging from 100 nm to 300 nm.

Most preferably, an immunogenic product comprising immunogenic protein heterocomplexes of the invention exclusively comprises carrier molecules associated to antigenic proteins, with the exclusion of any other material. More particularly, a heterocomplex of the invention does not comprise any other polymeric, proteinaceous or non proteinaceous material, other than the carrier and antigenic proteins characterizing it.

Recently, ZAGURY D et al. (2001, Proc. Nail. Acad. Sci. USA. 98(14):8024-8029), in a bibliographical study, suggested to induce an anti-cytokin immunity in patients in order to counteract the abnormal production in such pathologies of some cytokins, including interleukins, lymphokins, monokins, interferons, physiologically acting in the tissues, locally as a factor of programmed cell proliferation, differentiation, or death.

The above-mentioned authors state that the strategies of vaccine therapy were, until now, exclusively focused on the antigenic aggressor, whether it is a micro-organism, a cell or an allergen, but never attempted to fight the deregulation of cytokins induced under the effect of the aggressor. Said authors suggest an anti-cytokin vaccination as a prior step to a conventional vaccination having as an aim to neutralize or block the immunotoxic effect of the stroma, and to allow for the normal occurrence of the immune reaction adapted towards the antigenic aggressor.

Moreover, the Applicant's prior work, mentioned in the International Application published under WO 00/03732, showed that in the case of ATL leukemia, the neck of the uterus cancer and the Kaposi sarcoma, respectively, three proteins are involved in a local immunosuppression at the level of tumors or HIV1 infected cells:
the HTLV1 virus Tax protein,
the papillomavirus E7 protein, and
the V1H-1 virus Tat protein.

The Applicant also stated that some of such immunosuppressive proteins, such as the HIV1 Tat protein and the HPV E7 protein (Strains 16 and 18) also have activating effects on vascular endothelial cells.

They therefore suggested developing anti-cancer or anti-viral vaccines comprising a detoxicated immunogenic compound derivate of a protein coming from cancer cells, from virus infected cells or stroma immune cells, initially immunosuppressive and/or angiogenic with a local action, as, for example, a protein derived from the HIV1 virus Tat protein, the HTLV1 virus Tax protein, papillomavirus E7 protein as well as a mannan-depending lectin under an inactivated form.

Now, it has been shown according to the invention that the immunogenic product comprising immunogenic heterocomplexes such as hereinabove defined allows for the induction of a strong antibody response against the various above-mentioned deleterious antigenic molecules.

According to a first aspect, in the immunogenic heterocomplex of the invention, the antigenic protein(s) (i) consist(s) in cytokins naturally produced by said subject.

Preferably, the antigenic protein(s) (i) is/are selected from interleukin-4, alpha interferon, gamma interferon, VEGF, interleukin-10, alpha TNF, beta TGF, interleukin-5 and interleukin-6.

According to a second aspect, the antigenic protein(s) (i) making up an immunogenic heterocomplex of the invention is/are immunosuppressive or angiogenic proteins, or proteins derived from immunosuppressive or angiogenic proteins.

Preferably, the antigenic protein(s) (i) is/are selected amongst a papillomavirus E7 protein, the VIH 1 virus Tat protein, the HTLV 1 or HTLV 2 virus Tax protein, and the self p53 protein.

According to a third aspect, the antigenic protein(s) (i) making up an immunogenic heterocomplex according to the invention is/are proteins being toxic at a low dose to man or to a non human mammal. These are more particularly various proteins being lethal to man at a dose lower than 1 mg, lower than 100 µg, lower than 10 µg, even lower than 1 µg. These are predominantly toxic proteins able to be used for manufacturing so-called <<biological>> weapons, such as ricin, botulic toxins, *staphylococcus* enterotoxins, as well as an anthrax toxic protein (EF, LF, PA).

The carrier protein molecule (ii) included in an immunogenic protein heterocomplex of the invention could be a carrier molecule conventionally used in immunology, such as KLH, ovalbumin, bovine serum albumin (BSA), toxoid tetanos, B cholera toxin, etc.

Moreover, in an immunogenic product of the invention, the protein carrier molecule could be selected so as to induce or stimulate, besides the production of T helper lymphocytes, a cytotoxic and/or humoral immune response against itself, and its counterpart of native protein in the host organism, respectively through the activation of cytotoxic T lymphocytes and of B lymphocytes specific to such a carrier molecule.

Such a particular embodiment of an immunogenic product of the invention is particularly useful when there is simultaneously sought an efficient antibody response against an immunosuppressive or angiogenic deleterious protein, more particularly, for producing neutralizing or blocking antibodies, and a cell immune response generated by cytotoxic T lymphocytes raised against cells having at their surface the native antigen associated to Major Histocompatibility Complex (MHC) class I molecules, for example, an antigen of a pathogen, such as the VIH1 virus or a papillomavirus, or an antigen specifically expressed in cancer cells such as CEA, p53, Di12, etc.

Thus, according to this particular embodiment, the immunogenic product of the invention is characterized in that the carrier protein molecule (ii) is an immunogenic protein inducing, besides the production of T helper lymphocytes, the production of cytotoxic T lymphocytes raised against cells having at their surface said carrier protein molecule, or any peptide being derived therefrom, in association with Major Histocompatibility Complex (MHC) class I molecules and/or the production of antibodies by B lymphocytes raised against the carrier protein.

Thus, immunogenic products comprising immunogenic heterocomplexes of the invention are efficient immunologic means for the active therapeutic vaccination of an individual, whether a human mammal or a non human mammal, against a large variety of pathologies.

Illustrative examples of such immunogenic heterocomplex compositions contained in an immunogenic product according to the invention for preventing or treating, through an active therapeutic vaccination, various pathologies are mentioned hereinafter.

a) For preventing or treating AIDS:

Carrier protein molecule (ii): gp120, gp 160, p24, p17, nef or Tat proteins of HIV1 virus, detoxicated or stabilized if required, immunogenic fragments of such proteins as well as an immunogenic protein being derived therefrom (Zagury et al., 1998).

The mimotope gp120 protein could also be used as described by Fouts et al. (2000) and by Fouts et al. (2002).

Antigenic protein (i): Tat, IFNα, IL10 and TGFβ proteins, detoxicated if required, immunogenic fragments of such proteins, or an immunogenic protein being derived therefrom.

b) For preventing or treating the neck of uterus cancer:

Carrier protein molecule (ii): papillomavirus L1, L2 and E7 proteins, preferably a papillomavirus from strain 16 or 18, detoxicated or stabilized if required, immunogenic fragments of such proteins as well as an immunogenic protein being derived therefrom (Le Buanec et al., 1999).

Antigenic protein (i): E7, IFNα, IL10, TGFβ, TNFα and VEGF proteins, detoxicated or stabilized if required, immunogenic fragments of such proteins as well as an immunogenic protein being derived therefrom.

c) For preventing or treating ATL leukemia induced by the HTLV1 or 2 viruses:

Carrier protein molecule (ii): gp61 and HTLV1 or 2 virus Tax proteins, detoxicated if required, immunogenic fragments of such proteins as well as an immunogenic protein being derived therefrom (Cowan et al., 1997; Mori et al., 1996).

Antigenic protein (i): Tax, IL10, IFNα or TGFβ, TNFα, VEGF proteins, detoxicated if required, immunogenic fragments of such proteins as well as an immunogenic protein being derived therefrom.

d) For preventing or treating colon cancer:

Carrier protein molecule (ii): CEA and p53 proteins, detoxicated if required, immunogenic fragments of such proteins as well as an immunogenic protein being derived therefrom (Zusman et al., (1996)).

Antigenic protein (i): IFNα, TGFβ, IL10, FasL and VEGF proteins, detoxicated if required, immunogenic fragments of such proteins as well as an immunogenic protein being derived therefrom.

e) For preventing or treating breast cancer:

Carrier protein molecule (ii): Di12 protein, immunogenic fragments of such a protein as well as an immunogenic protein being derived therefrom (Yoshiji et al., 1996).

Antigenic protein (i): IFNα, TGFβ, IL10, FasL and VEGF proteins, detoxicated if required, immunogenic fragments of such proteins as well as an immunogenic protein being derived therefrom.

f) For preventing or treating pancreas cancer:

Carrier protein molecule (ii): CaSm protein, detoxicated if required, immunogenic fragments of such proteins as well as an immunogenic protein being derived therefrom.

Antigenic protein (i): VEGF and TNFα proteins, detoxicated or stabilized if required, immunogenic fragments of such proteins as well as an immunogenic protein being derived therefrom.

g) For preventing or treating prostate cancer:

Carrier protein molecule (i): OSA and ETS2 proteins, detoxicated or stabilized if required, immunogenic fragments of such proteins as well as an immunogenic protein being derived therefrom. (Sementchenko V I et al., 1998).

Antigenic protein (i): IL6 and TGFβ proteins, detoxicated or stabilized if required, immunogenic fragments of such proteins as well as an immunogenic protein being derived therefrom (Adler et al., 1999).

h) For preventing or treating some allergies:

Carrier protein molecule (ii): it is selected amongst molecular allogens, such as Bet v 1 (birch-tree pollen), Der p 1 (acarid) and Fel d 1 (cat) proteins, their immunogenic peptide fragments as well as an immunogenic protein being derived therefrom. The Bet v 1 antigen is described more particularly by Ferreira et al. (1993), the Der p 1 antigen is described, in particular, by Tovey et al. (1981) and the Fel d 1 antigen is described, more particularly by Morgensterm et al. (1991)

Antigenic protein (i): it induces the production of neutralizing or blocking antibodies raised against the IL4 cytokin factor, being mainly produced by T lymphocytes of Th2 type, orienting the humoral immune response towards the production of IgE isotype antibodies. According to another embodiment, the antigenic protein (i) induces the production of neutralizing or blocking antibodies against the IL5 cytokin factor, being mainly produced by T lymphocytes of Th2 type.

According still another embodiment, preventing allergy could occur by means of an immunogenic product inducing an antibody response against the main basophil granulation effector, i.e. IgE isotype antibodies. For this purpose, the invention provides an immunogenic product comprising (i) an IgE isotype human antibody and (ii) the VIH1 inactivated Tat protein.

i) For the prevention against lethal proteins used in biological weapons

Also, an immunogenic product according to the invention could be used for immunizing individuals against numerous toxic products used, in particular, in chemical and biological weapons, as for example, ricin.

Amongst the most toxic proteins against which an immunization, mainly through the production of antibodies, is being sought, botulic toxins, ricin, *staphylococcus* enterotoxins, *Clostridium perfringens* toxins and anthrax toxic proteins.

Generally speaking, for producing an immunogenic product according to the invention, wherein the antigenic protein (i) is a highly toxic protein of the above-mentioned type, a previously detoxicated protein is used under the form of a toxoid. For detoxicating the protein, before its use for producing an immunogenic product according to the invention, various methods could be used, and preferably one of the following methods consisting in:

a) treating the native toxic protein by glutaraldehyde;

b) treating the native toxic protein through the combined action of formol and glutaraldehyde; or c) if need be, through chemical modification of His and Tyr groups by means of appropriate reagents, for example, through carboxymethylation of such amino acid residues.

For preventing the lethal action of toxins originating from *Bacillus anthracis*, as proteins, antigenic proteins (i), a detoxicated protein originating from an anthrax protein selected amongst EF (<<Edema Factor>>), LF (<<Lethal Factor>>) and PA (<<Protective Antigen>>) proteins are used preferably.

For preventing the lethal actions of proteins originating from *Clostridium perfringens*, as the antigenic protein (i), a detoxicated protein originating from the Epsilon toxin of *Clostridium perfringens* are preferably used.

For preventing the lethal action of toxins originating form *Clostridium botulinum*, as antigenic proteins (i), a detoxicated protein originating from a botulic toxin selected amongst A, B, C, D, E, F and G toxins being naturally synthetized in the form a single 150 kDa polypeptide chain as well as the $H_c$ fragment of such botulinic toxins, said fragment $H_c$ having a molecular mass of approximately 50 kDa, are preferably used.

For producing inactivated botulic toxins, the man of the art could use techniques known per se, more particularly those used for preparing the anterior vaccine compositions, such as those described by Fiock et al. or by Siegel et al. (Fiock, M. A., Cardella, M. A., Gearinger, N. F., J. Immunol., 1963, 90, 697-702; Siegel, L. S., J. Clin. Microbiol., 1988, 26, 2351-2356).

For preventing the lethal action of toxins originating from ricin seed (*Ricinus communis*), as the antigenic protein (i), a detoxicated protein originating from the ricin toxin, preferably the β fragment of ricin, is preferably used.

Thus, the invention also provides an immunogenic product comprising (i) the β fragment of ricin and (ii) the KLH protein.

For purifying ricin, the man of the art could use any known technique, such as those described by Osborne et al., Kabat et al. or Kunnitz et al. (Osborne, T. B., Mendel, L B. and Harris, J. F.: Amer. J. Physiol., 1905, 14, 259-269; Kabat, E. A. Heidelberger, M. and Bezer, A. E.: J. Biol. Chem., 1947, 168, 629-; Kunnitz, M. and McDonald, M.: J. Gen. Physiol., 1948, 22,25-Moulé, Y.: Bull. Soc. Chim. Biol., 1951, 33, 1461-1467). He could also make use of the affinity chromatography purification techniques described by Tomila et al., Nicolson et al. or Olsnes et al. (Tomila, M., Kurokawa, T., Onozaki, K. et a/.,: Experientia, 1972, 28, 84-85; Nicolson, G. L. and Blaustein, J.: J. Biochim. Biophys. Acta, 1972, 266, 543-547; Olsnes, S., Salvedt, E. and Pihl, A.: J. Biol. Chem., 1974, 249, 803-810). The ricin A and B chains could be purified as described by Hedge et al. (Hedge, R. and Podder, S. K.,: Eur. Biochem., 1998, 254, 596-601).

For preventing the lethal action of toxins originating from *staphylococcus* and more particularly from *Staphylococcus aureus*, as the antigenic protein (i), a detoxicated protein originating from a toxin selected amongst SEA (<<Staphylococcal Enterotoxin A>>), SEB (<<Staphylococcal Enterotoxin B>>), SEC (<<Staphylococcal Enterotoxin C>>), SED (<<Staphylococcal Enterotoxin D>>), SEE (<<Staphylococcal Enterotoxin E>>), SEG (<<Staphylococcal Enterotoxin G>>), SEH (<<Staphylococcal Enterotoxin H>>), SEI (<<Staphylococcal Enterotoxin I>>) and TSST-1 (<<Toxic Shock Syndrome Toxin-1>>) is preferably used.

The above listed enterotoxins could be prepared by the man of the art by means of techniques described in the listed work below, relating to the description of each of such toxins.

SEA is synthesized in the form of a precursor enterotoxin with 257 amino acids (Huang, I. Y., Hughes, J. L, Bergdoll, M. S. and Schantz, E. J. J Biol. Chem. 1987, 262, 7006-7013). The mature toxin with a molecular mass equal to 27,100 Da derives from the precursor toxin through the loss of a N-terminal hydrophobic leader sequence with 24 amino acid residues (Betley, M. J. and Mekalanos, J. J. J Bacteriol., 1998, 170. 34-41). SEA exists under 3 different isoforms through their IP.

The SEB precursor protein comprises 267 amino acids (Mr=31,400 Da) with a N-terminal signal peptide with 27 amino acids. Its binding site to the receptor of T cells (<<T-Cell Receptor>> or <<TCR>>) encompasses the shallow cavity, whereas the class II MHC molecule is fixed on an adjacent site (Kappler, J. W., Herman, A., Clements, J. and Marrack, P.: J. Exp. Med., 1992, 175, 387-396; Papageorgiu, A. C., Trauter, H. S. and Acharya, K. R. J Mol. Biol., 1998, 277, 61-79; Soos, J. M. and Johnson, H. M. Biochem. Biophys. Res. Commun., 1994, 201, 596-602).

SEC possesses 3 antigenically distinct sub-types: SEC 1, SEC 2 et SEC 3. The precursor proteins contains 267 amino acid residues (Houde, C. J., Hackett, S. P. and Bohach, G. A. Mol. Gen. Genet., 1990, 220, 329-333) with a signal peptide with 27 amino acid residues (Bohach, G. A. and Schlievert, P. M.: Infect. Immun., 1989, 57, 2243-2252).

SED is made up of 258 amino acid residues with a signal peptide of 30 amino acid residues. Its three-dimension structure is similar to the structure of other bacterial superantigens.

SEE having a 26,000 Da molecular mass have 81% of AA sequence homology with SEA.

SEG is made up of 233 amino acid residues (Munson, S. H., Tremaine, M. T., Betley, M. J. and Welch, R. A.: Infect. Immun., 1998, 66, 3337-3348).

SEH has a 27,300 Da molecular mass (Su, Y. C. and Wong, A. C.: Apll. Environ. Microbiol., 1995, 61, 1438-1443). It does not have any crossed immunologic reaction with other enterotoxins.

SEI has a sequence comprising 218 amino acid residues. This is the toxin with the lowest homology level with other enterotoxins SEJ made up of 269 amino acid residues has a high AA sequence homology with SEA, SEE and SED (64-66%).

Preferably, an immunogenic product according to the invention comprises, in combination, several antigenic proteins (i) each derived from an above-mentioned toxic protein, for example, 2, 3, 4 or 5 antigenic proteins (i) each derived from an above listed toxic protein.

For example, an immunogenic product according to the invention for preparing a vaccine composition intended for preventing the toxicity of *staphylococcus* enterotoxins preferably comprises 2, 3, 4 or 5 antigenic proteins (i) each derived from a *staphylococcus* enterotoxin.

According to a particular embodiment of an immunogenic product according to the invention, wherein the antigenic protein(s) (i) is/are derived from highly toxic proteins for man, the carrier protein is the KLH protein.

Thus, according to a first particular aspect of an immunogenic product of the invention, wherein the carrier protein molecule both induces the production of auxiliary T lymphocytes (<<T helper>>), of cytotoxic T lymphocytes and of B lymphocytes specific to the carrier protein molecule, said carrier protein molecule (ii) is selected amongst the papillomavirus L1, L2, and E7 proteins.

Thus, according to a second particular aspect of an immunogenic product of the invention, wherein the carrier protein molecule induces, in addition to the production of auxiliary T lymphocytes (<<T helper>>), the differentiation of cytotoxic T lymphocytes and of B lymphocytes specific to the carrier protein molecule, said carrier protein molecule (ii) is selected amongst the HIV1 virus gp160, p24, p17, Nef and Tat proteins.

Thus, according to a third particular aspect of an immunogenic heterocomplex of the invention, wherein the carrier protein molecule both induces the production of auxiliary T lymphocytes (<<T helper>>), of cytotoxic T lymphocytes and of B lymphocytes specific to the carrier protein molecule, said carrier protein molecule (ii) is selected amongst CEA, p53, Di12, CaSm, OSA and ETS2 proteins.

According to a fourth particular aspect of an immunogenic product of the invention, wherein the carrier protein molecule induces, in addition to the differentiation of auxiliary T lymphocytes (<<T helper>>), the production of antibodies raised against the carrier protein molecule, said carrier protein molecule (ii) is selected amongst Bet v 1, Der p 1 and Fel d 1 proteins.

In an immunogenic product according to the invention, the immunogenic protein heterocomplexes are selected amongst the following heterocomplexes, where the antigenic proteins (i), on the one hand, and the protein carrier molecule (ii), on the other hand, are respectively:

a) (i) IL-4 and (ii) KLH;
b) (i) alpha interferon and (ii) KLH;
c) (i) VEGF and (ii) KLH;
d (i) IL-10 and (ii) KLH;
e) (i) alpha interferon and (ii) gp 160 of VIH1;
f) (i) IL-4 and (ii) the Bet v 1 allergenic antigen; and
g) (i) VEGF and (ii) the papillomavirus E7 protein;
h) (i) the inactivated VIH1 Tat protein and (ii) the VIH1 gp120 protein;
i) i) an IgE isotype human antibody and (ii) the inactivated VIH1 Tat;
j) (i) the ricin (3 fragment and (ii) KLH.

Method for Preparing an Immunogenic Product Comprising Immunogenic Protein Heterocomplexes of the Invention Another object of the invention is also a method for preparing an immunogenic product comprising the hereinabove defined immunogenic heterocomplexes, characterized in that it comprises the following steps of:

a) incubating the antigenic proteins (i) and the carrier molecule (ii) in a molar ratio (i):(ii) ranging from 10:1 to 50:1 in the presence of a binding chemical agent;

b) collecting the immunogenic product comprising immunogenic heterocomplexes being prepared in step a).

Preferably, the binding chemical agent is glutaraldehyde.

Most preferably, the method is further characterized in that step a) is followed by a stabilizing step of the product comprising the immunogenic heterocomplexes by formaldehyde, prior to step b) for recovering the heterocomplexes.

Preferably, when glutaraldehyde is used as the binding chemical agent, it is present in the coupling reaction medium in a final concentration ranging between 0.002M and 0.03M, advantageously between 0.02M and 0.03M, preferably in a final concentration of 0.026M.

The coupling reaction with glutaraldehyde advantageously occurs for 20 minutes to 60 minutes, preferably 30 minutes, at a temperature ranging from 20 to 25° C.

After the coupling step, the excess glutaraldehyde is removed, for example, through dialysis by means of a dialysis membrane with a 3 kDa cutoff threshold. The dialysis step advantageously occurs at 4° C. in a buffer adjusted to pH 7.6.

For stabilizing the product comprising the protein heterocomplexes as prepared in step a), said product could be treated in solution by the formaldehyde, for example, by formaldehyde in a final concentration of 3 mM. The stabilization reaction is advantageously performed for 12 to 48 hours, preferably between 20 and 30 hours, and most preferably, for 24 hours. The stabilization reaction using the formaldehyde is advantageously stopped through the addition of glycine, preferably in a 0.1M concentration, for 1 hour and at a temperature ranging from 20 to 25° C.

The Compositions Comprising an Immunogenic Product Comprising Immunogenic Protein Heterocomplexes of the Invention Another object of the present invention is also to provide a composition comprising an immunogenic product such as hereinabove defined.

The invention also relates to a pharmaceutical composition comprising a protein immunogenic product such as hereinabove defined.

Another object of the invention is an immunogenic composition characterized in that it comprises, as the active ingredient, an immunogenic product as hereinabove defined, in association with one or more physiologically compatible excipients.

It also relates to a vaccine composition characterized in that it comprises, as the active ingredient, an immunogenic product as hereinabove defined, in association with one or more physiologically compatible excipients.

Depending on the target objectives, systemic adjuvants or mucosal adjuvants are being used. For example, a mucosal adjuvant is preferably used for preventing the epithelial tissue cancers and preferably systemic adjuvants are used for preventing or treating virus infections such as HIV1 and HTLV1 as well as for preventing or treating allergies.

Amongst systemic adjuvants, those of the IFA type are preferably used (Incomplete Freund's Adjuvant), as well as calcium phosphate or alumina hydroxide.

Amongst mucosal adjuvants, those preferably used are like B chloratoxin (CTB) or a mutant of the LT toxin (LTµ).

According to a particular aspect, an immunogenic composition according to the invention also comprises one or more immuno-stimulating agents, in combination with an immunity adjuvant, such as for example, the CpG immuno-stimulating agent well known in the state of the art.

It has indeed been shown according to the invention that the use of the CpG adjuvant, and more particularly the CpG adjuvant wherein the intra-chain bonds between nucleotides consist in phosphorothioate bonds to stimulate the simultaneous production of IgG and IgA isotype antibodies, after a systemic administration.

It also relates to a mucosal or systemic vaccine, characterized in that it comprises, as the active ingredient, an immunogenic product such as hereinabove defined, in association with one or more excipients, including physiologically compatible adjuvants.

The immunogenic compositions or the vaccines according to the present invention are useful for example in the treatment, both curative and preventive, of cancers, more particularly, of cancers induced by viruses such, as for example, the ATL (Acute T cell leukemia) caused by the HTLV1, or the neck of uterus cancer caused by the papillomavirus, as well as the Burkitt lymphoma as well as the Kaposi sarcoma caused by the viruses from the herpes family, respectively the Epstein-Barr (EBV) and the HHV8 as well as in treatment of AIDS or for preventing or treating allergic reactions.

The immunogenic products according to the invention could be used as follows.

To a patient, is administered, under a form adapted to the systemic or mucosal administration, an immunogenic product comprising immunogenic protein heterocomplexes according to the present invention, for example, intranasally, in a sufficient amount to be therapeutically efficient, to a subject in need of such a treatment. The dose to be administered could range for example from 10 to 1000 µg intranasally, once a week for 2 months and then, given the transitory character of the antibody response directed against the antigen of interest, periodically depending on the serum antibody rate, for example, once every 2 to 6 months.

Two or more different immunogenic products could be administered in one single preparation for inducing neutralizing antibodies in all the deleterious functional sites should one single molecule not carry all the active sites of the overproduced toxin or cytokin which is to be neutralized.

As for drugs, the immunogenic products of the invention could be incorporated into pharmaceutical compositions adapted for an administration through the systemic route or an administration through the mucosal route, including the oromucosal route, more particularly, the intranasal route, the oral route and the vaginal route. The administration could be performed in one single dose or a dose repeated once or several times after some time interval.

This is why the present application has also as an object a pharmaceutical, curative, or preventive composition, characterized in that it comprises as an active ingredient, one or more immunogenic products such as hereinabove defined. The immunogenic product could be packaged alone or mixed with an excipient or a mixture of pharmaceutically acceptable excipients such as an adjuvant. Amongst the excipients adapted for the intranasal or oral route, are particularly to be selected the capryl caproyl macrogol glycerides as LABRASOL® from the GATTEFOSSE corporation or alumina hydroxide (ALHYDRAGEL, SUPERFOS, Denmark).

For the oral administration according to the invention, the active ingredient will be associated to a mucosal immunity adjuvant, such as a CT, LT or CTB mutant.

Galenic forms are particularly well suited, as described by Boyaka et al. <<Strategies for mucosal vaccine development>> in Am. J. Trop. Med. Hyg. 60(4), 1999, pages 35-45. Are also to be mentioned gastro resistant, more particularly bioadhesive microgranules, such as described by Rojas et al. in Pharmaceutical Research, vol. 16, n°2, 1999, page 255.

Under the particular implementing conditions, an above-mentioned vaccine pharmaceutical composition will be selected, characterized in that it comprises a mucosal immunity adjuvant, such a CT mutant (cholera toxin) or a LT mutant *E. coli* labile enterotoxin).

Under other particular implementing conditions, a vaccine pharmaceutical composition will be selected, characterized in that it contains an adjuvant absorbing the active ingredient, such as alumina hydroxide or gold particles.

Another object of the present invention is a method for preparing a composition as described hereinabove, characterized in that are mixed, using methods known per se, the active immunogenic product(s) with the acceptable excipients, including pharmaceutical acceptable ones and if need be, with a systemic or mucosal immunity adjuvant.

Under preferred implementing conditions of the above-mentioned method, bioadhesive and gastroresistant microgranules are prepared for the digestive route containing the immunogenic active ingredients and, if need be, the adjuvants.

The present invention is further illustrated by the following examples.

EXAMPLES

Examples of Heterocomplex Preparations

Example 1

Preparation of Murine KLH-VEGF Heterocomplex 0.58 mg of KLH protein is dissolved in 0.5 ml of 10 mM phosphate buffer, pH 8.5. To this solution is added 1 mg of murine VEGF dissolved in 1 ml of the same buffer.

The thus obtained protein mixture is treated using glutaraldehyde in the final concentration of 0.026 M for 30 minutes at room temperature.

The excess glutaraldehyde is then removed by 3 successive 2 hour dialyses, each performed in a dialysis tube with a cutoff threshold being 3 kDa, at 4° C., against 200 ml of phosphate buffer, pH 7.6 10 mM.

The mixture is then treated using formaldehyde at the final concentration of 33 mM for 24 hours. Then the reaction is blocked by the addition of final 0.1 M glycine for 1 hour at room temperature.

The mixture is finally dialyzed under the same conditions as the previously performed dialysis.

Example 2

Human KLH-VEGF Heterocomplex

Such a heterocomplex is the active ingredient of a vaccine able to mainly induce in the vaccinee the production of antibodies neutralizing the human VEGF.

0.58 mg of KLH protein is dissolved in 0.5 ml of 10 mM phosphate buffer, pH 8.5. To this solution is added 1 mg of human VEGF dissolved in 1 ml of the same buffer.

The thus obtained protein mixture is treated using glutaraldehyde in the final concentration of 0.026 M for 30 minutes at room temperature.

The excess glutaraldehyde is then removed by 3 successive 2 hour dialyses, each performed in a dialysis tube with a cutoff threshold being 3 kDa, at 4° C., against 200 ml of phosphate buffer, pH 7.6 10 mM.

The mixture is then treated using formaldehyde at the final concentration of 33 mM for 24 hours. Then the reaction is blocked by the addition of final 0.1 M glycine for 1 hour at room temperature. The mixture is finally dialyzed under the same conditions as the previously performed dialysis.

Example 3

Preparation of Murine KLH-IL4 Heterocomplex 0.841 mg of KLH protein is dissolved in 0.8 ml of 10 mM phosphate buffer, pH 8.5. To this solution is added 1 mg of murine IL4 dissolved in 1 ml of the same buffer.

The thus obtained protein mixture is treated using glutaraldehyde in the final concentration of 0.026 M for 30 minutes at room temperature.

The excess glutaraldehyde is then removed by 3 successive 2 hour dialyses, each performed in a dialysis tube with a cutoff threshold being 3 kDa, at 4° C., against 200 ml of phosphate buffer, pH 7.6 10 mM.

The mixture is then treated using formaldehyde at the final concentration of 33 mM for 24 hours. Then the reaction is blocked by the addition of final 0.1 M glycine for 1 hour at room temperature. The mixture is finally dialyzed under the same conditions as the previously performed dialysis.

Example 4

Preparation of a Human KLH-IL4 Heterocomplex

Such a heterocomplex is the active ingredient of a vaccine able to mainly induce in the vaccinee the production of antibodies neutralizing the human IL4.

1 mg of KLH protein is dissolved in 1 ml of 10 mM phosphate buffer, pH 8.5. To this solution is added 1 mg of murine IL4 protein dissolved in 1 ml of the same buffer.

The thus obtained protein mixture is treated using glutaraldehyde in the final concentration of 0.026 M for 30 minutes at room temperature.

The excess glutaraldehyde is then removed by 3 successive 2 hour dialyses each performed in a dialysis tube with a cutoff threshold being 3 kDa, at 4° C., against 200 ml of phosphate buffer, pH 7.6 10 mM.

The mixture is then treated using formaldehyde at the final concentration of 33 mM for 24 hours. Then the reaction is blocked by the addition of final 0.1 M glycine for 1 hour at room temperature. The mixture is finally dialyzed under the same conditions as the previously performed dialysis.

Example 5

Preparation of a KLH-IFNα Complex

Such a conjugate is the active ingredient of a vaccine able to mainly induce in the vaccinee the production of antibodies neutralizing the human IFNα.

0.625 mg of KLH protein is dissolved in 0.6 ml of 10 mM phosphate buffer, pH 8.5. To this solution is added 1 mg of human IFNα protein dissolved in 1 ml of the same buffer.

The thus obtained protein mixture is treated using glutaraldehyde in the final concentration of 0.026 M for 30 minutes at room temperature.

The excess glutaraldehyde is then removed by 3 successive 2 hour dialyses, each performed in a dialysis tube with a cutoff threshold being 3 kDa, at 4° C., against 200 ml of phosphate buffer, pH 7.6 10 mM.

The mixture is then treated using formaldehyde at the final concentration of 33 mM for 48 hours. Then the reaction is blocked by the addition of final 0.1 M glycine for 1 hour at room temperature. The mixture is finally dialyzed under the same conditions as the previously performed dialysis.

Example 6

Preparation of a gp160-IFNα Complex

Such a heterocomplex is the active ingredient of a vaccine able to induce in the vaccinee the production of antibodies neutralizing both the gp160 structure protein of the HIV-1 virus and the immunosuppressive IFNα cytokin protein. Moreover, such a heterocomplex should be able to induce a cell reaction (chemiokins, auxiliary T, CTL) raised against the infected cells expressing the gp160.

0.380 mg of gp160 protein is dissolved in 0.380 ml of 10 mM phosphate buffer, pH 8.5. To this solution is added 1 mg of human IFNα protein dissolved in 1 ml of the same buffer.

The thus obtained protein mixture is treated using glutaraldehyde in the final concentration of 0.026 M for 30 minutes at room temperature.

The excess glutaraldehyde is then removed by 3 successive 2 hour dialyses each performed in a dialysis tube with a cutoff threshold being 3 kDa, at 4° C., against 200 ml of phosphate buffer, pH 7.6 10 mM.

The mixture is then treated using formaldehyde at the final concentration of 33 mM for 48 hours. Then the reaction is blocked by the addition of final 0.1 M glycine for 1 hour at room temperature. The mixture is finally dialyzed under the same conditions as the previously performed dialysis.

Example 7

Preparation of a gp160-Toxoid Tat Heterocomplex (the Tat Protein is Biochemically Inactivated Such a heterocomplex is the active ingredient of a vaccine able to induce in the vaccinee the production of antibodies neutralizing both the gp160 structure protein of the HIV-1 virus and the extracellular Tat protein of VIH-1. Moreover, such a complex should be able to induce a cell reaction (chemiokins, auxiliary T, CTL) raised against the infected cells expressing the gp160.

0.550 mg of gp120 protein is dissolved in 0.550 ml of 10 mM phosphate buffer, pH 8.5. To this solution is added 1 mg of toxoid Tat protein dissolved in 1 ml of the same buffer.

The thus obtained protein mixture is treated using glutaraldehyde in the final concentration of 0.026 M for 30 minutes at room temperature.

Then the reaction is blocked by the addition of final 0.1 M glycine for 1 hour at room temperature. The excess glycine is then removed by 3 successive 2 hour dialyses each in a dialysis tube with a 3 kDa cutoff threshold, at 4° C. against 200 ml of phosphate buffer, pH 7.6, 10 mM.

Example 8

Preparation of a gp160-GM Tat Heterocomplex (the Tat Protein is Genetically Inactivated)

Such a heterocomplex is the active ingredient of a vaccine able to induce in the vaccinee the production of antibodies neutralizing both the gp160 structure protein of the HIV-1 virus and the Tat protein regulating the VIH-1. Moreover, such a heterocomplex should be able to induce a cell reaction (chemiokins, auxiliary T, CTL) raised against the infected cells expressing the gp160.

0.550 mg of gp160 protein is dissolved in 0.550 ml of 10 mM phosphate buffer, pH 8.5. To this solution is added 1 mg of GM Tat protein dissolved in 1 ml of the same buffer.

The thus obtained protein mixture is treated using glutaraldehyde in the final concentration of 0.026 M for 30 minutes at room temperature.

Then the reaction is blocked by the addition of final 0.1M glycine for 1 hour at room temperature. The excess glycine is then removed by 3 successive 2 hour dialyses each performed in a dialysis tube with a cutoff threshold being 3 kDa, at 4° C., against 200 ml of phosphate buffer, pH 7.6 10 mM.

Example 9

Preparation of Murine KLH-TNFα Heterocomplex

Such a conjugate is the active ingredient of a vaccine able to mainly induce in the vaccinee the production of antibodies neutralizing the murine TNFα.

0.625 mg of KLH protein is dissolved in 0.6 ml of 10 mM borate buffer, pH 8.8, 150 mM NaCl. To this solution is added 1 mg of human TNFα protein dissolved in 1 ml of the same buffer.

The thus obtained protein mixture is treated using glutaraldehyde in the final concentration of 0.026 M for 45 minutes at room temperature.

The excess glutaraldehyde is then removed by 3 successive 4 hour dialyses each performed in a dialysis tube with a cutoff threshold being 3 kDa, at 4° C., against 200 ml of phosphate buffer, pH 7.6 10 mM 150 mM NaCl.

The mixture is then treated using formaldehyde at the final concentration of 33 mM for 48 hours. Then the reaction is blocked by the addition of final 0.1M glycine for 1 hour at room temperature. The mixture is finally dialyzed under the same conditions as the previously performed dialysis.

Example 10

Preparation Heterocomplex $(19\text{-}50)\text{-}_n\text{IgE}$

The Tat peptide (19-50) brings auxiliary helper epitopes.
Sequence of the Tat peptide to be used:
Lys-Thr-Ala-Cys-Thr-Asn-Cys-Tyr-Cys-Lys-Lys-Cys-Cys-Phe-His-Cys-Gln-Val-Cys-Phe-Ile-Thr-Lys-Ala-Leu-Gly-Ile-Ser-Tyr-Gly-Arg-Lys (SEQ ID NO: 1).

Such a conjugate is the active ingredient of a vaccine able to mainly induce in the vaccinee the formation of (human) anti-IgE antibodies.

0.1 mg of Tat peptide (19-50) ($4.06\times10^{-8}$ mole) are dissolved in 0.2 ml of 10 mM borate buffer, pH 8.5. To this solution is added 1 mg of human IgE ($6.6\times10^{-9}$ mole) dissolved in 1 ml of the same buffer.

The thus prepared mixture is then treated using formaldehyde at the final concentration of 0.026 M for 30 minutes at room temperature.

The excess glutaraldehyde is then removed by 2 successive 4 hour dialyses and a final 16 hour dialysis against a large volume of phosphate buffer, 10 mM, pH 7.4 containing 0.8% of NaCl (PBS), at 4° C., using a dialysis bag with a cutoff threshold being at 10 kDa. (IgE peptide ratio=50:1)

Example 11

Preparation of a Heterocomplex Against the Ricin Fragment

Such a heterocomplex is the active ingredient of a vaccine able to induce in the vaccinee the formation of neutralizing antibodies directed against the fragment involved in the binding of the ricin molecule, thereby preventing it from exerting its toxic activity.

To 0.5 mg of KLH ($1.1\times10^{-3}$ mole) dissolved in 0.5 ml of 10 mM phosphate buffer, pH 8.2, is added 1 mg ($3.3\times10^{-8}$ mole) of a fragment of ricin dissolved in 1 ml of the same buffer. The thus prepared mixture is treated using formaldehyde at the final concentration of 0.026 M for 30 minutes at room temperature.

The excess glutaraldehyde is then removed by 2 successive 4 hour each dialyses and a 16 hour dialysis against a large volume of phosphate buffer, 10 mM, containing 0.8% of NaCl (PBS), using a dialysis bag with a cutoff threshold being 3 kDa. (KLH:Ricin-a ratio=1:30).

Examples of Biochemical Characterizations of Heterocomplexes

A. Material and Methods of Examples 12 to 23

The biochemical characterizations of heterocomplexes are performed by means of the following techniques:

1. Antigenicity Test

The study of antigenicity of a heterocomplex compared to the antigenicity of proteins making it up is performed by a conventional indirect ELISA. Such a technique allows for a protein to be quantitatively measured through the specific recognition of an antibody raised against an antigen. Such a test comprises depositing sample dilutions containing the sought protein in wells of a microtiter plate. A specific polyclonal antibody reacts with the immobilized protein. A second antibody, conjugated with horseradish peroxydase, specific to the first one is then added. The formed complex is revealed through incubation with OPD. The resulting yellow colour is directly proportional to the amount of bound proteins. The absorbance (DO) of each well is measured by means of a microplate reader. The amount of protein present in the sample is then determined by means of a calibrating range.

2. Isoelectrofocusing in Agarose Gel Followed by a Western Blot

The isoelectrofocusing in agarose gel allows to separate molecules depending on their isoelectric point (Ip) under non denaturing conditions, allowing to study heterocomplexes without destroying the weak bonds existing within such complexes.

The isofocusing is followed by an emergence through a Western blot. After electrophoretic separation, the molecules are transferred on a nitrocellulose membrane through capillarity. Such molecules are then characterized by immunochemistry.

3. Measurement of the Percentage of Molecules of the Antigen of Interest Covalently Linked to the Carrier Protein Molecule (First Method)

Estimating the percentage of molecules of the antigen of interest covalently linked to carrier protein molecules in an immunogenic product occurs, for example, through molecular sieving on a column containing Superdex 200, under denaturing (8 M urea) and reducing (5% beta-mercaptoethanol) conditions.

The % of covalently linked molecules of the antigen of interest is deducted from the amount of antigen of interest (determined by a conventional indirect ELISA) present in the exclusion volume of the column. Indeed, the carrier protein molecule, such as KLH, having a molecular mass much higher than the highest fractionating limit of the column being used (200 kDa in this case), exists in the exclusion volume of such a column. Thus, under denaturing and reducing conditions, only the antigens of interest covalently linked to the carrier protein molecule exist in the exclusion volume.

4. Measurement of the Percentage of Molecules of the Antigen of Interest Covalently Linked to the Carrier Protein Molecule (Second Method)

The percentage of cytokin fixed on the carrier protein (KLH) was determined by a double sandwich ELISA, by means of a capture antibody specifically directed against the carrier protein.

100 μl of horse polyclonal antibodies raised against KLH (1 mg/ml) diluted in a 10 mM phosphate buffer, pH 7.3 NaCl 150 mM (PBS) are bound in wells of a microtiter plate (high-binding COSTAR) for 2 hours at 37° C. After 3 washes in PBS/0.1% TWEEN 20 (PBST), the wells are saturated with PBS containing 2% of BCS.

After 1.30 hour of saturation, the wells are washed three times with PBST, then heterocomplex 2 by 2 dilutions (10, 5, 2.5, 1.25, 0.625, 0.312 and 0.156 μg/ml) made in duplicate, are added in the wells (100 μl/well).

After 2 hours of incubation, the wells are washed three times with PBST. The TWEEN, a dissociating agent, present in the washing buffer, allows to remove all the molecules which are not covalently linked to the KLH being, itself, specifically bound on the capture antibody.

Then, both heterocomplex dilutions are treated in two different ways:

a) the first set is incubated with an antibody raised against KLH b) the second set is incubated with an antibody raised against cytokin.

After 1.30 hour of incubation at 37° C., the wells are washed as previously indicated then incubated with a secondary antibody coupled to the peroxydase, directed against the origin species of the first antibody. After 1.30 hour of incubation at 37° C., the antibodies are washed again. Then, the addition of the peroxydase substrate, O-PhenyleneDiamine (OPD) allows for the revelation of the presence of the KLH bound by the capture antibody and cytokins covalently bound on the KLH.

The amount of KLH bound by the capture antibody and then the amount of cytokin molecules covalently bound on the KLH are calculated by means of calibrating curves done by ELISA.

The percentage of cytokin covalently bound to the KLH is then determined.

Example 12

Biochemical Characterization of the KLH-Murine VEGF Heterocomplex

1. Antigenicity
The KLH-murine VEGF heterocomplex has an antigenicity identical to the antigenicity of murine VEGF.

2. Isoelectrofocusing in Agarose Gel Followed by a Western Blot
FIG. 1 shows that the KLH-murine VEGF heterocomplex migrates under the form of a single strip with a Ip different from the native molecules making it up.

Example 13

Biochemical Characterization of the KLH-Human VEGF Heterocomplex

1. Antigenicity
The KLH-human VEGF heterocomplex has an antigenicity identical to the antigenicity of human VEGF.

Figure 2:
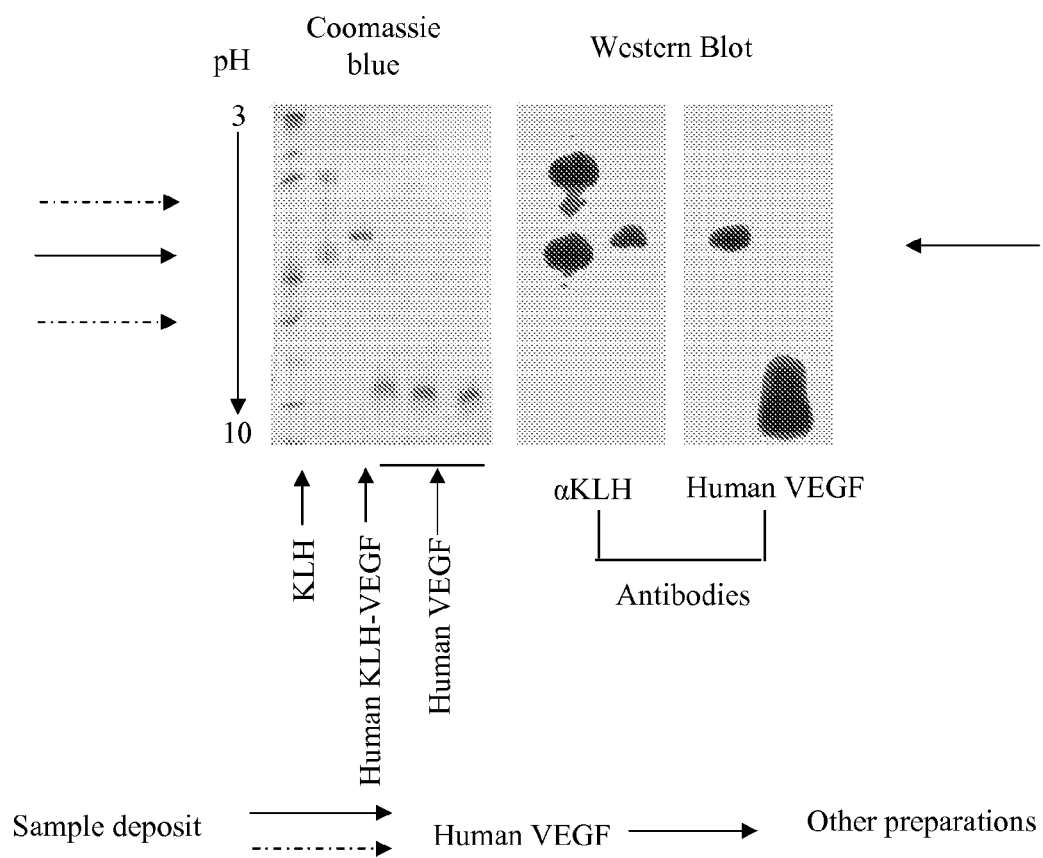
FIG. 2 illustrates the characterization of the immunogenic product comprising human KLH-VEGF heterocomplexes through isoelectrofocusing through a colouration with Coomassie blue, followed by an immunoblotting (<<Western Blot>>). The isoelectrofocusing gel is represented at the left of the figure. The immunoblotting gels using anti-KLH (left) or human anti-VEGF (right) antibodies are illustrated on the right of the figure.

2. Isoelectrofocusing Followed by a Western Blot
FIG. 2 shows that the KLH-human VEGF heterocomplex migrates under the form of a single strip with a Ip different from the native molecules making it up. The human VEGF sample was deposited at three different locations in order to show that it still migrates at the same location.

Example 14

Biochemical Characterization of KLH-Murine IL4 Heterocomplex

1. Antigenicity
The KLH-murine IL4 heterocomplex has an antigenicity identical to the antigenicity of murine IL4.

Example 15

Biochemical Characterization of the KLH-Human IL4 Heterocomplex

1. Antigenicity
The human KLH-IL4 complex has an antigenicity equal to the antigenicity of the human IL4 protein.

Figure 3:
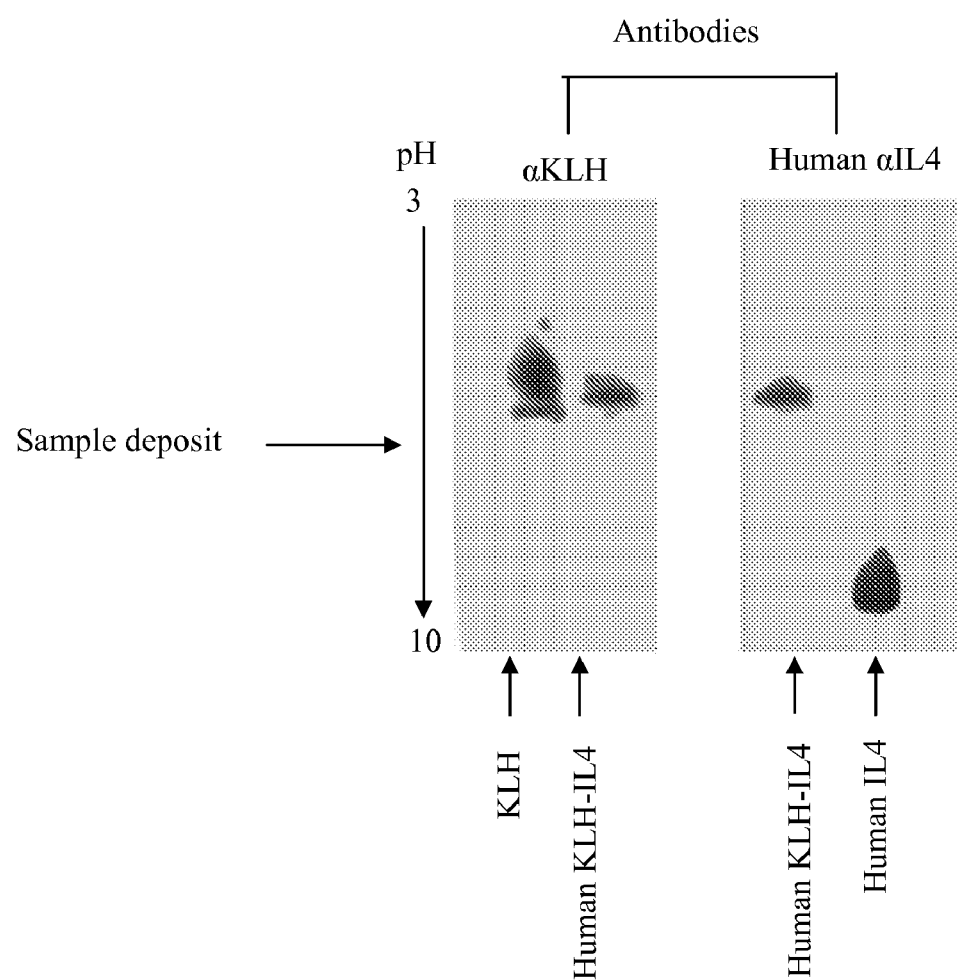
FIG. 3 illustrates the characterization of the immunogenic product comprising human KLH-IL4 heterocomplexes through isoelectrofocusing in an agarose gel followed by the emergence of proteins through immunoblotting (<<Western Blot>>).

2. Isoelectrofocusing Followed by a Western Blot
FIG. 3 shows that the human KLH-IL4 heterocomplex migrates under the form of a single strip with a Ip different from the native molecules making it up.

Example 16

Biochemical Characterization of the KLH-IFNα Heterocomplex

1. Antigenicity
The human KLH-IFNα complex has an antigenicity identical to the antigenicity of the human IFNα.

2. Estimation of the Percentage of Molecules of the Antigen of Interest Covalently Linked to the Carrier Protein Molecule
The KLH-IFNα preparation is passed on a superdex S200 column following the above described conditions. The apparent peak in the exclusion volume was collected, dialyzed then freeze-dried. The concentration in antigen of interest was determined by the indirect ELISA technique. The IFNα amount present in the excluded volume is 30 μg while 1000 μg of IFN were used for preparing the immunogenic product, without any measurable loss of antigen during the preparing method. The percentage of molecules of the antigen of interest covalently linked to the KLH molecule in the immunogenic product comprising KLH-IFNα heterocomplexes can therefore be estimated to approximately 3%.

Example 17

Biochemical Characterization of the gp160-IFNα Heterocomplex

1. Antigenicity
The human gp160-IFNα complex has an antigenicity identical to the antigenicity of the gp 160 protein as well as to that of human IFNα.

Figure 4:
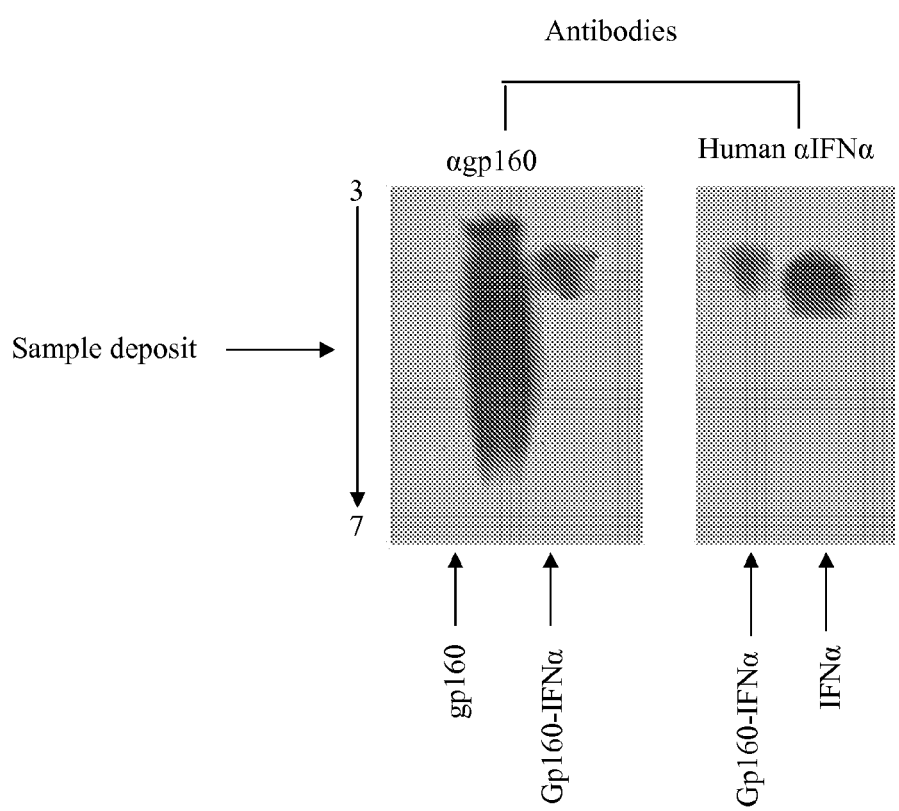
FIG. 4 illustrates the characterization of the immunogenic product comprising gp 160-IFNα complexes through isoelectrofocusing in an agarose gel followed by the mergence of proteins through immunoblotting (<<Western Blot>>).

2. Isoelectrofocusing Followed by a Western Blot
FIG. 4 shows that the human gp160-IFNα heterocomplex migrates under the form of one single strip at a Ip being quite different from the Ip of the gp160 protein recombining the component. The Ip of such a heterocomplex is slightly lower than that of IFNα.

Example 18

Biochemical Characterization of the gp160-Toxoid Tat Heterocomplex

1. Antigenicity
The gp160-toxoid Tat complex has an antigenicity identical to the antigenicity of the gp160 protein and to that of the Tat protein.

Example 19

Biochemical Characterization of the gp160-GM Tat Heterocomplex

1. Antigenicity

The gp160-GM Tat complex has an antigenicity identical to the antigenicity of the gp160 protein and to that of the Tat protein.

Example 20

Biochemical Characterization of the KLH-Murine IL4 Heterocomplex

1. Antigenicity

The murine KLH-IL4 heterocomplex has an antigenicity identical to the antigenicity of murine IL4.

2. Estimation of the % of Antigen Molecules of Interest Covalently Bound to the Carrier Protein Molecule 11% of molecules of murine IL4 are covalently fixed to the KLH.

Example 21

Biochemical Characterization of the KLH-IFNα Heterocomplex

1. Antigenicity

The KLH-human IFNα complex has an antigenicity identical to the antigenicity of the human IFNα.

2. Estimation of the % of Antigen Molecules of Interest Covalently Fixed to the Carrier Protein Molecule 8% of molecules of human IFNα are covalently bound to the KLH.

Example 22

Biochemical Characterization of the Tat-$_h$IgE Peptide Heterocomplex

1. Antigenicity

The Tat-$_h$IgE peptide complex has an antigenicity comparable to that of human IgE.

Example 23

Biochemical Characterization of the KLH-β Ricin-Heterocomplex

1. Antigenicity

The KLH-β Ricin complex has an antigenicity comparable to that of the β ricin fragment.

2. Isoelectrofocusing Followed by a Western Blot

The complex migrates under the form of a single strip and the presence of the β fragment is enhanced by Western Blot.

Examples of Immunogenic Activity of Heterocomplexes

Example 24

Immunogenic Activity of the KLH-Murine VEGF Heterocomplex

A. Material and Methods

The immunogenic (humoral) of the KLH-murine VEGF preparation compared to that of the murine VEGF was studied in 18 to 20 g balb c mouse.

1—Immunization

At days 0, 7, 14, 21, a group of 8 mice receives a 0.1 ml (10 μg) injection of an AIF emulsion through the intramuscular route. A 5 booster injection in AIF is given at D60.

A blood sample at the retro-orbital level is taken from each mouse before the first injection at d-2.

3 control mice receive the same preparations without any immunogen.

The mice are sacrificed 12 days after the last immunization.

2—Toxicity

The abnormal toxicity is studied in 3 mice receiving one human dose (50 μg) according to the pharmacopeia.

The lack of immunotoxicity of the heterocomplex is evaluated in vitro by cell proliferation test conducted on PBMCs cultivated in the presence of the complex and stimulated by PPD or toxoid tetanos.

B. Results

1. Lack of Toxicity of the Heterocomplex In Vivo and In Vitro

The mice immunized both with the KLH-murine VEGF preparation and the murine VEGF only do not show any clinical sign and no anatomic wound. The immunosuppression test shows that doses of 100 ng/ml to 1 μg/ml of KLH-murine VEGF do not reduce the proliferation of lymphocytes.

None of the three mice immunized with 50 μg of the heterocomplex show any sign of toxicity (temperature, cutaneous disorders, systemic or regional signs) during the 7 days following the injection.

2—Humoral Response

Figure 5:
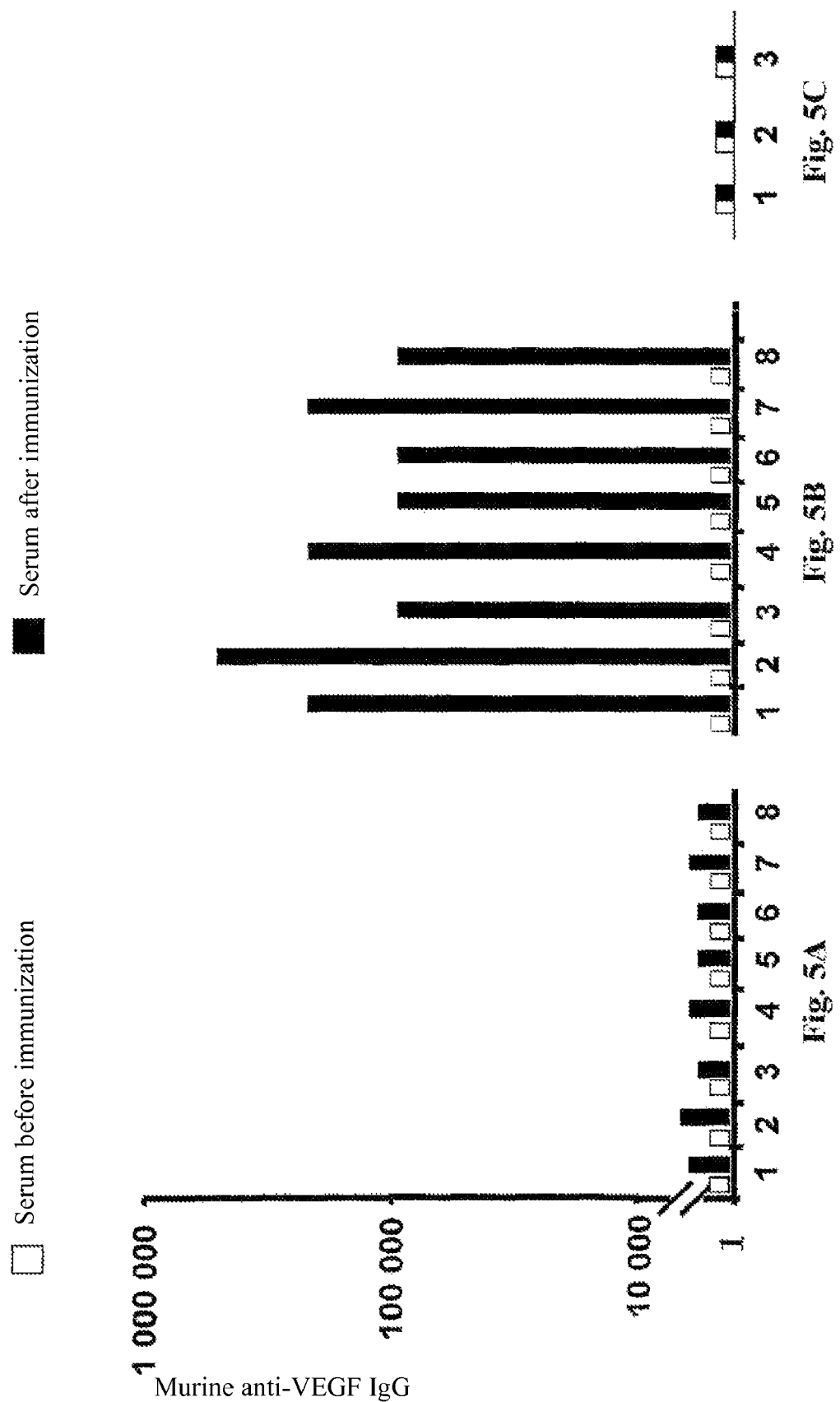
FIG. 5 illustrates the immunogenic (humoral) activity of the murine KLH-VEGF immunogenic product through determination of the title antibody obtained after an immunization of mice.

The humoral response is measured by the presence in the serum of antibodies of the IgG type directed against the murine VEGF, determined by ELISA and expressed in titer (opposite of the dilution giving an optical density higher than 0.3). FIG. 5 shows the resulting antibody titers.

The mice immunized with the KLH-murine VEGF preparation show higher antibody titers of the IgG type than those of mice immunized with the murine VEGF only.

Figure 6:
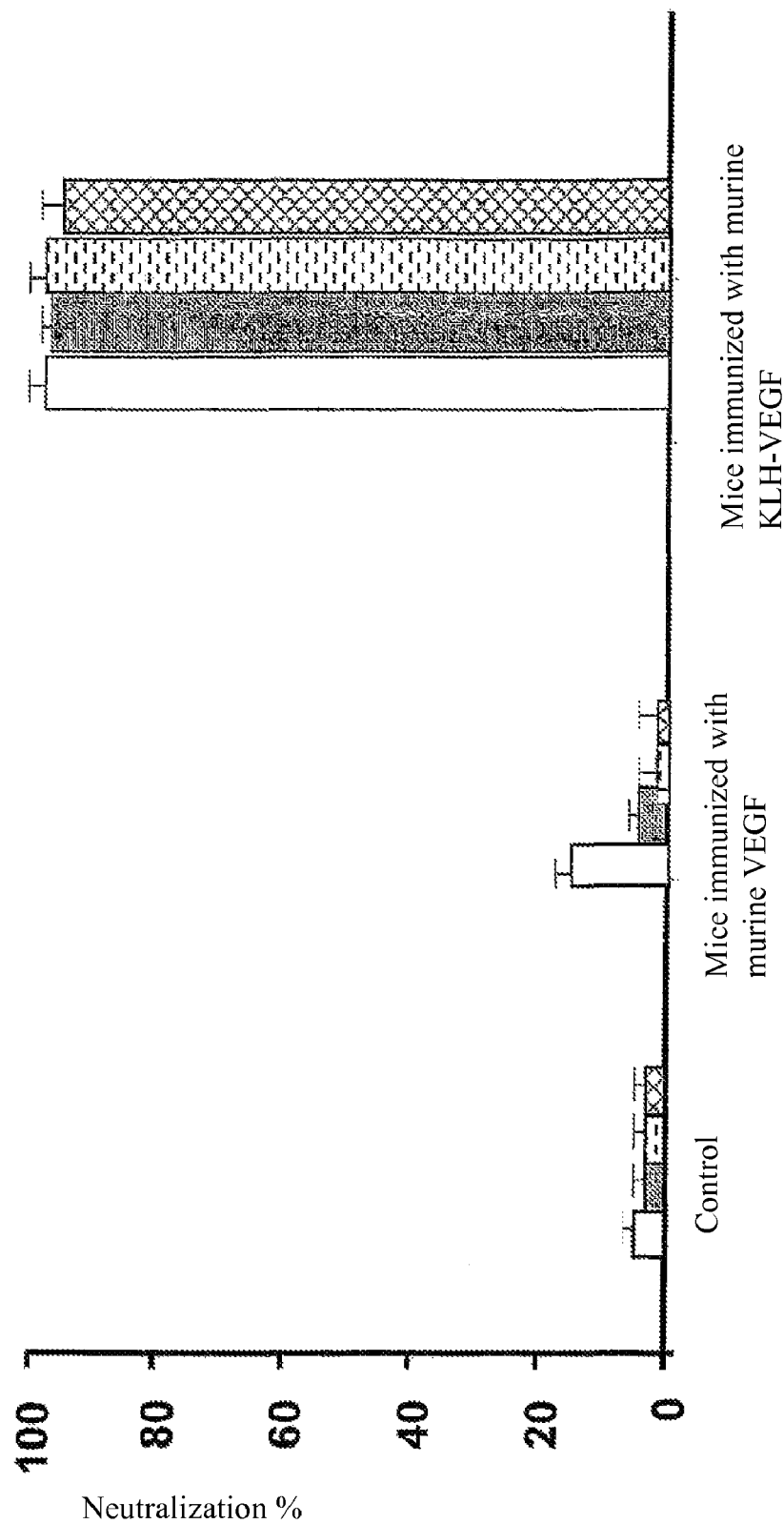
FIG. 6 shows the immunogenic (humoral) activity of the murin KLH-VEGF immunogenic product, through determination of the neutralizing power of antibodies obtained after immunization, towards the angiogenic activity of the VEGF protein.

The neutralizing activity of such antibodies was measured by means of the biological activity test of VEGF, selective growth factor of endothelial cells. Endothelial cells (HU-VECs) are cultivated in flat bottom wells of a microculture plate at a level of 3,000 cells per well. The sera of each group of mice were pooled. Different dilutions of such serum pools (1/100-1/800) taken at D-2 and D72 were pre-incubated for 2 hours with 20 ng/ml of murine VEGF then deposited on such endothelial cells. The cell culture continued at 37° C. in a humid atmosphere loaded with 5% of CO2 for 3 days. 18 hours before the end of the incubation, 0.5 μCi of titered thymidine/well were added. The neutralizing sera prevent the murine VEGF from inducing the proliferation of endothelial cells, while non neutralizing sera allow for the proliferation of such cells. The results are expressed in neutralization percentage. FIG. 6 shows the obtained results.

The antibodies induced by the complex have a higher neutralizing power than that induced by the murine VEGF.

Example 25

Immunogenic Activity of the KLH-Human VEGF Heterocomplex

A. Material and Methods

The immunogenic (humoral) of the KLH-human VEGF preparation compared to that of the human VEGF was studied in 18 to 20 g balb c mouse.

1—Immunization

At days 0, 7, 14, 21, a group of 8 mice receives a 0.1 ml (10 μg) injection of an AIF emulsion through the intramuscular route. A 5 μg booster injection in AIF is given at D60.

A blood sample at the retro-orbital level is taken from each mouse before the first injection at d-2.

3 control mice receive the same preparations without an immunogen.

The mice are sacrificed 12 days after the last immunization.

2—Toxicity

The abnormal toxicity is sought in 3 mice receiving one human dose (50 µg) according to the pharmacopeia.

The lack of immunotoxicity of the heterocomplex is evaluated in vitro by a cell proliferation test conducted on PBMCs cultivated in the presence of the complex and stimulated by PPD or toxoid tetanos.

B. Results

1—Lack of Toxicity of the Heterocomplex In Vivo and In Vitro

The mice immunized both with the murine KLH-VEGF preparation and the murine VEGF only do not show any clinical sign and no anatomic wound. The immunosuppression test shows that doses of 100 ng/ml to 1 µg/ml of KLH-human VEGF do not reduce the proliferation of lymphocytes.

None of the three mice immunized with 50 µg of the heterocomplex show any sign of toxicity (temperature, cutaneous disorders, systemic or regional signs) during the 7 days following the injection.

2—Humoral Response

Figure 7:
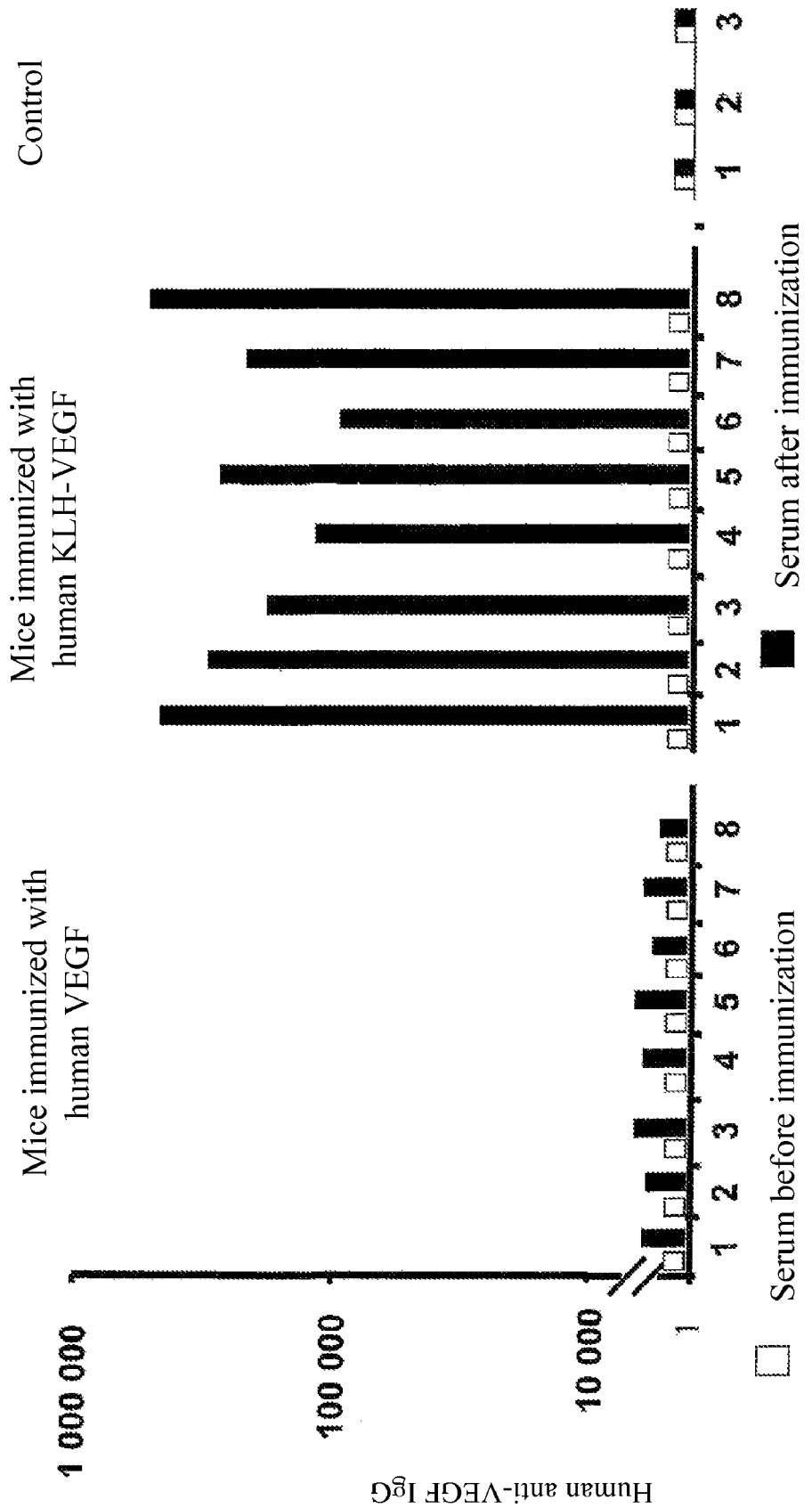
FIG. 7 illustrates the immunogenic (humoral) activity of the human KLH-VEGF immunogenic product, through determination of the antibody title obtained after immunization of mice.

The humoral response is measured by the presence in the serum of antibodies of the IgG type raised against the human VEGF, determined by ELISA and expressed in titer (opposite of the dilution giving an optical density higher than 0.3). FIG. 7 shows the resulting antibody titers.

The mice immunized with the KLH-human VEGF preparation show higher antibody titers of the IgG type than those of mice immunized with the human VEGF only.

Figure 8:
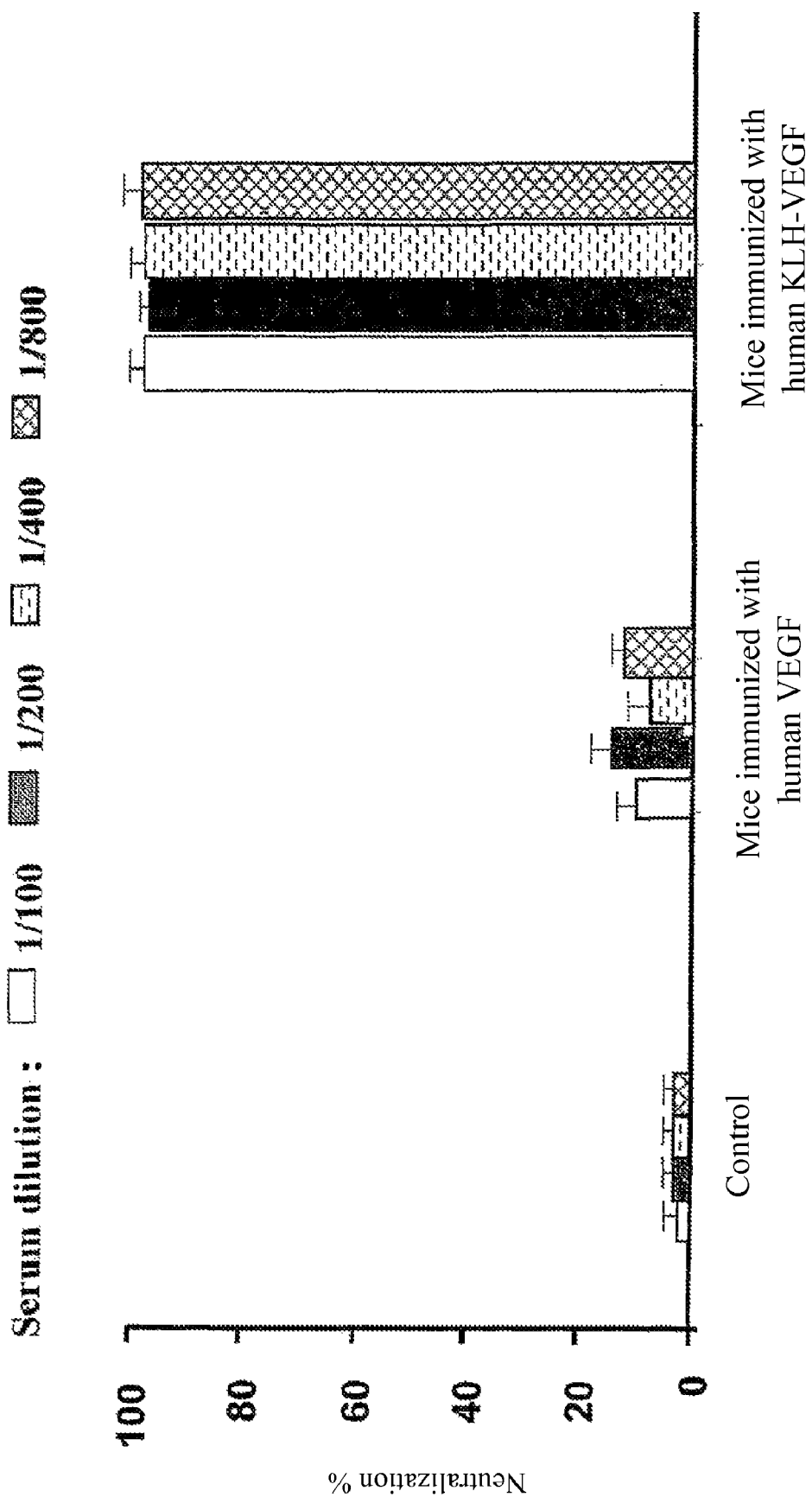
FIG. 8 illustrates the immunogenic (humoral) activity of the human KLH-VEGF immunogenic product, through determination of the neutralizing power of antibodies obtained after immunization, towards the angiogenic activity of the VEGF protein, measured through the proliferation of endothelial cells.

The neutralizing activity of such antibodies was measured by means of the biological activity test of VEGF, selective growth factor of endothelial cells. Endothelial cells (HU-VECs) are cultivated in flat bottom wells of a microculture plate at a level of 3,000 cells per well. The sera of each group of mice were pooled. Different dilutions of such serum pools (1/100-1/800) taken at D-2 and D72 were pre-incubated for 2 hours with 20 ng/ml of human VEGF then deposited on such endothelial cells. The cell culture is continued at 37° C. in a humid atmosphere loaded with 5% of CO2 for 3 days. 18 hours before the end of the incubation, 0.5 µCi of titered thymidine/well were added. The neutralizing sera prevent the human VEGF from inducing the proliferation of endothelial cells, while non neutralizing sera allow for the proliferation of such cells. The results are expressed in neutralization percentage. FIG. 8 shows the obtained results.

The antibodies induced by the complex have a higher neutralizing power than that induced by the human VEGF.

Example 26

Immunogenic Activity of the KLH-Murine IL4 Heterocomplex

A. Material and Methods

The immunogenic (humoral) activity of the murine KLH-IL4 preparation compared to that of the murine IL4 was studied in 18 to 20 g balb c mouse.

1—Immunization

At days 0, 7, 14, 21, a group of 8 mice receives a 0.1 ml (10 µg) injection of an AIF emulsion through the intramuscular route. A 5 µg booster injection in AIF is given at D60.

A blood sample at the retro-orbital level is taken from each mouse before the first injection at D-2 and D72.

3 control mice receive the same preparations without an immunogen.

14 days after the last immunization, the control mice and the mice immunized with the KLH-murine IL4 were challenged with birch-tree pollen in the presence of alum (100 µg/mice) through the subcutaneous route at D74, D95 and D109. Blood samples are regularly taken in order to follow the occurrence of class G and E antibodies raised against Bet v 1, a major allergen of the birch-tree pollen.

2—Toxicity

The abnormal toxicity is sought in 3 mice receiving one human dosis (50 µg) according to the pharmacopeia.

The lack of immunotoxicity of the heterocomplex is evaluated in vitro by a cell proliferation test conducted on PBMCs cultivated in the presence of the complex and stimulated by PPD or toxoid tetanos.

B. Results

1. Lack of Toxicity of the Heterocomplex In Vivo and In Vitro

The mice both immunized with the KLH-murine IL4 preparation and the murine IL4 only do not show any clinical sign and no anatomic wound. The immunosuppression test shows that doses of 100 ng/ml to 1 µg/ml of KLH-murine IL4 do not reduce the proliferation of lymphocytes.

None of the three mice immunized with 50 µg of the heterocomplex show any sign of toxicity (temperature, cutaneous disorders, systemic or regional signs) during the 7 days following the injection.

2—Humoral Response

Figure 9:
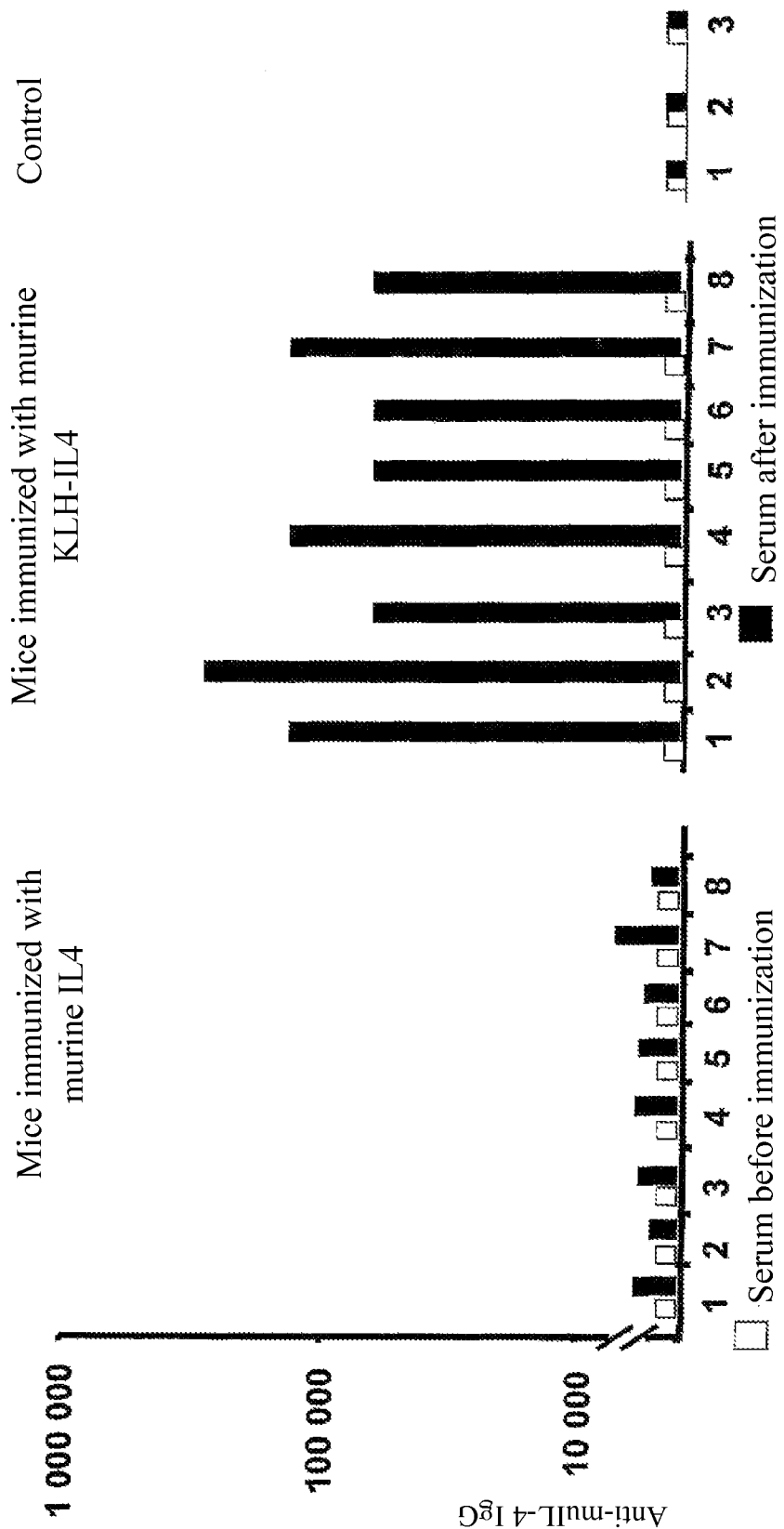
FIG. 9 illustrates the immunogenic (humoral) activity of the murine KLH-IL4 immunogenic product, through determination of the title antibody obtained after immunization.

The humoral response is measured by the presence in the serum of antibodies of the IgG type raised against the murine VEGF, determined by ELISA and expressed in titer (opposite of the dilution giving an optical density higher than 0.3). FIG. 9 shows the resulting antibody titers.

The mice immunized with the KLH-murine IL4 preparation show higher antibody titers of the IgG type than those of mice immunized with the murine IL4 only.

Figure 10:
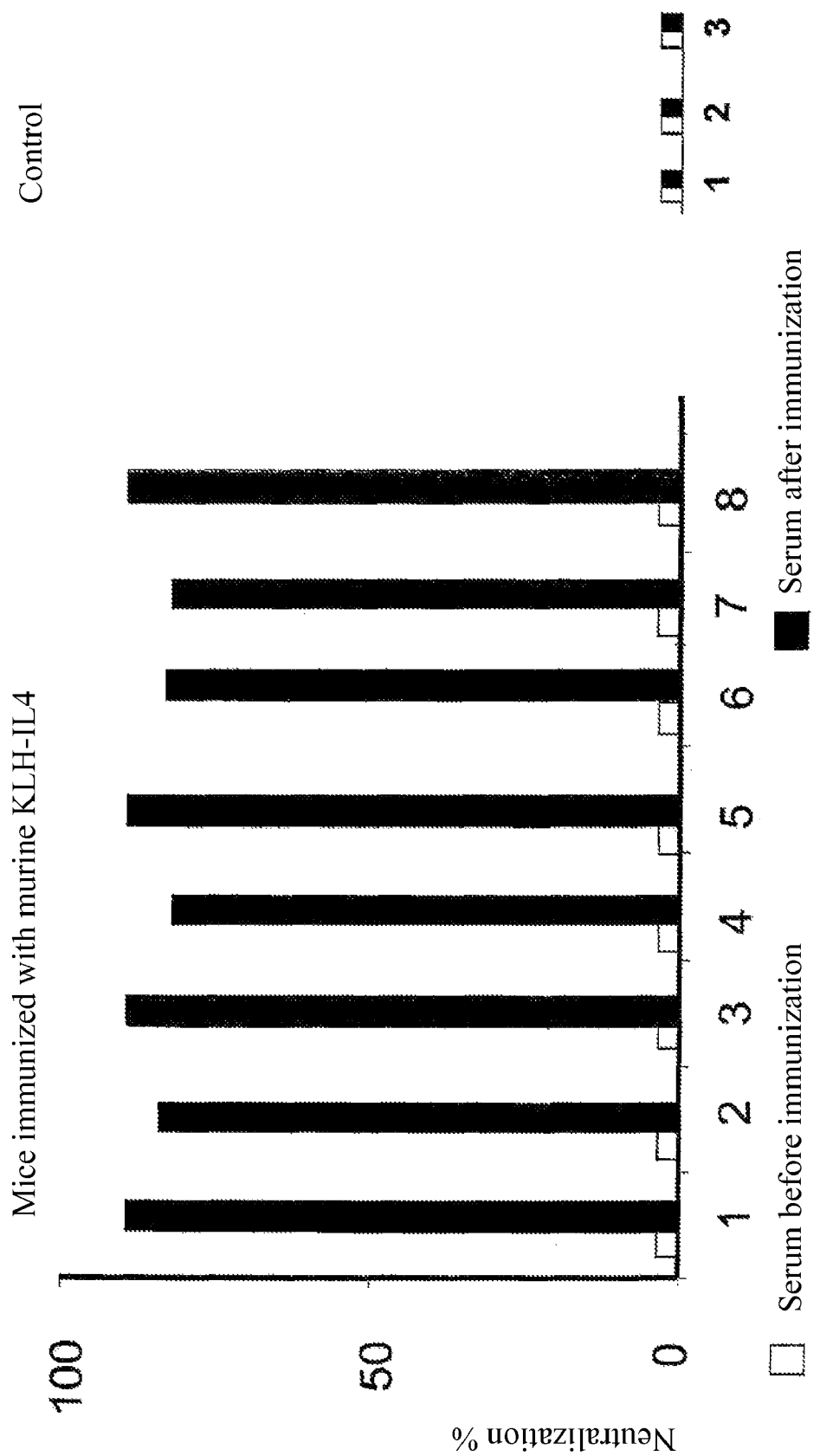
FIG. 10 illustrates the immunogenic (humoral) activity of the murine KLH-IL4 immunogenic product, through determination of the neutralizing power of antibodies obtained after immunization, towards the inducing activity of the proliferation of HT-2 cells by the IL4.

The neutralizing activity of those antibodies present in mice immunized with the KLH-murine IL4 preparation was measured by means of the biological activity test of the murine IL4. This test uses HT-2 cells, murine cell lineages the growth of which is IL4 murine-dependent (Watson, J. 1979. J. Exp. Med. 150:1510.). Endothelial cells HT-2 are cultivated in round bottom wells of a microculture plate at a level of 10,000 cells per well. Sera diluted at 1/50 taken at D-2 and D72 are pre-incubated for 2 hours with 50 ng/ml of murine H4 then deposited on HT-2 cells. The cell culture is continued at 37° C. in a humid atmosphere loaded with 5% of CO2 for 3 days. 4 hours before the end of the incubation, 0.5 µCi of titered thymidine/well were added. The neutralizing sera prevent the murine IL4 from inducing the proliferation of HT-2 cells, while non neutralizing sera allow for the proliferation of such cells. The results are expressed in neutralization percentage. FIG. 10 shows the obtained results.

The antibodies induced by the complex are neutralizing.

Figure 11:
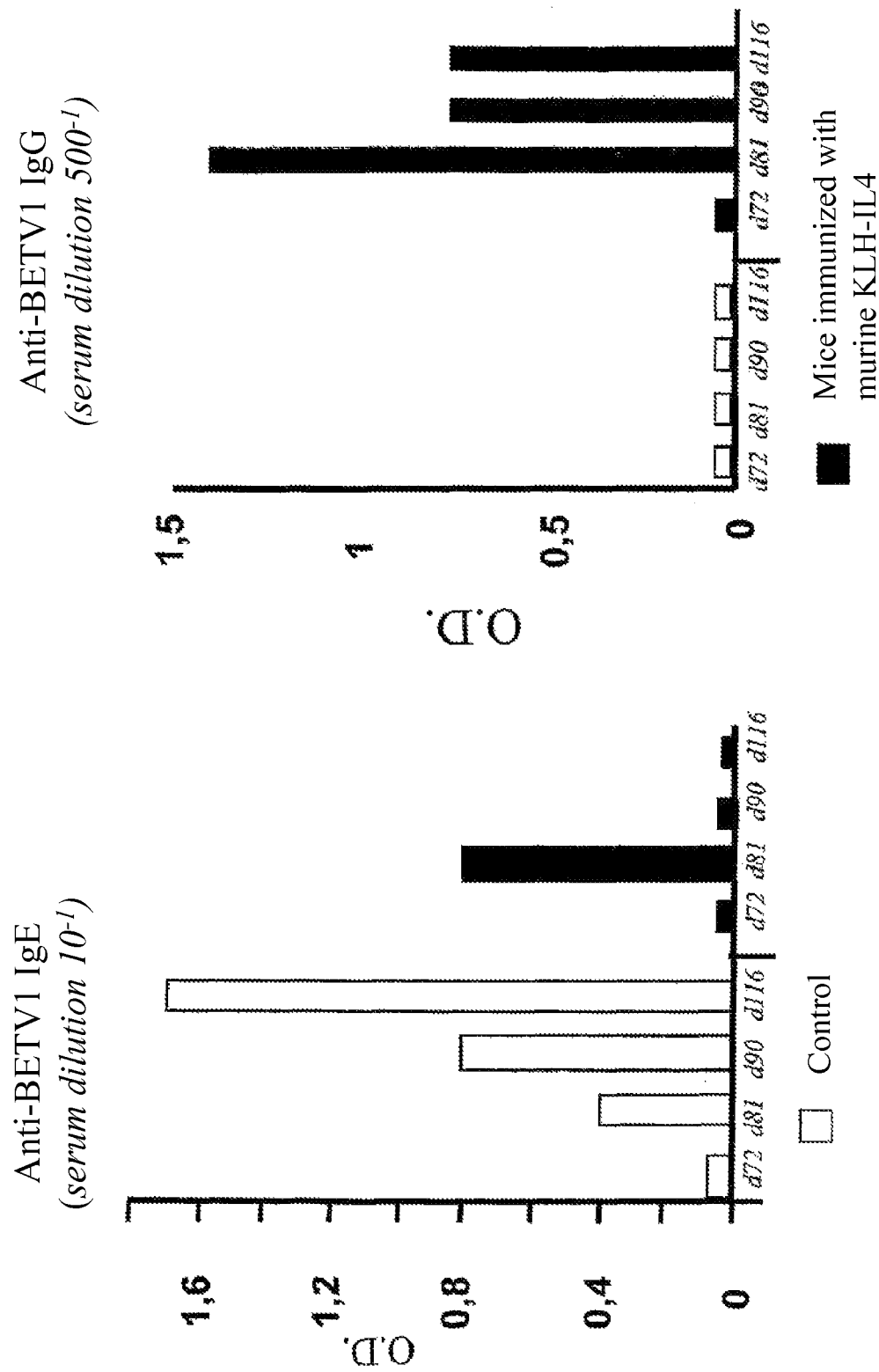
FIG. 11 illustrates the results of the production of the IgG and IgE class antibodies raised against Bet v 1, after the injection of birch-tree pollen, to mice preliminarily immunized with an immunogenic product according to the invention comprising KLH-IL4 complexes.

Moreover, such neutralizing antibodies raised against murine IL4 prevent the production, by those mice, of antibodies of the IgE type raised against Bet v 1, when the latter are challenged with birch-tree pollen. FIG. 11 indeed shows that mice immunized with KLH-murine IL4 have neutralizing IgGs raised against murine NL4 blocking the production of IgE raised against Bet v 1 and start to produce antibodies of the IgG type directed against Bet v 1. On the other hand, mice which did not receive any murine KLH-IL4 and therefore not having any antibodies of the IgG type directed against IL4, only produce antibodies of the IgE type directed against Bet v 1.

Example 27

Immunogenic Activity of the KLH-Human IL4 Heterocomplex

A. Material and Methods

The immunogenic (humoral) of the KLH-human HA preparation compared to that of the human IL4 was studied in 18 to 20 g balb c mouse.

1—Immunization

At days 0, 7, 14, 21, a group of 3 mice receives a 0.1 ml (10 µg) injection of an AIF emulsion through the intramuscular route. A 5 µg booster injection in AIF is given at D60.

A blood sample at the retro-orbital level is taken from each mouse before the first injection at d-2.

3 control mice receive the same preparations without an immunogen.

The mice are sacrificed 12 days after the last immunization.

2—Toxicity

The abnormal toxicity is sought in 3 mice receiving one human dosis (50 µg) according to the pharmacopeia.

The lack of immunotoxicity of the heterocomplex is evaluated in vitro by a cell proliferation test conducted on PBMCs cultivated in the presence of the complex and stimulated by PPD or toxoid tetanos.

B. Results

1. Lack of Toxicity of the Heterocomplex In Vivo and In Vitro

The mice both immunized with the KLH-human IL4 preparation and the human IL4 only do not show any clinical sign and no anatomic wound. The immunosuppression test shows that doses of 100 ng/ml to 1 µg/ml of KLH-human IL4 do not reduce the proliferation of lymphocytes.

None of the three mice immunized with 50 µg of the heterocomplex show any sign of toxicity (temperature, cutaneous disorders, systemic or regional signs) during the 7 days following the injection.

2—Humoral Response

The humoral response is measured by the presence in the serum of antibodies of the IgG type directed against the human IL4, determined by ELISA and expressed in titer (opposite of the dilution giving an optical density higher than 0.3).

TABLE 1

| Titer | | |
|---|---|---|
| D-2 | | D72 |
| Control mice: | | |
| Control mouse 1 | $<500^{-1}$ | $<500^{-1}$ |
| Control mouse 2 | $<500^{-1}$ | $<500^{-1}$ |
| Control mouse 3 | $<500^{-1}$ | $<500^{-1}$ |
| Mice immunized with human IL4: | | |
| mouse 4 | $<500^{-1}$ | $32,000^{-1}$ |
| mouse 5 | $<500^{-1}$ | $48,000^{-1}$ |
| mouse 6 | $<500^{-1}$ | $16,000^{-1}$ |
| Mice immunized with the KLH-human IL4 complex: | | |
| mouse 7 | $<500^{-1}$ | $256,000^{-1}$ |
| mouse 8 | $<500^{-1}$ | $128,000^{-1}$ |
| mouse 9 | $<500^{-1}$ | $128,000^{-1}$ |

The mice immunized with the KLH-human IL4 preparation show higher antibody titers of the IgG type than those of mice immunized with the human IL4 only.

Figure 12:
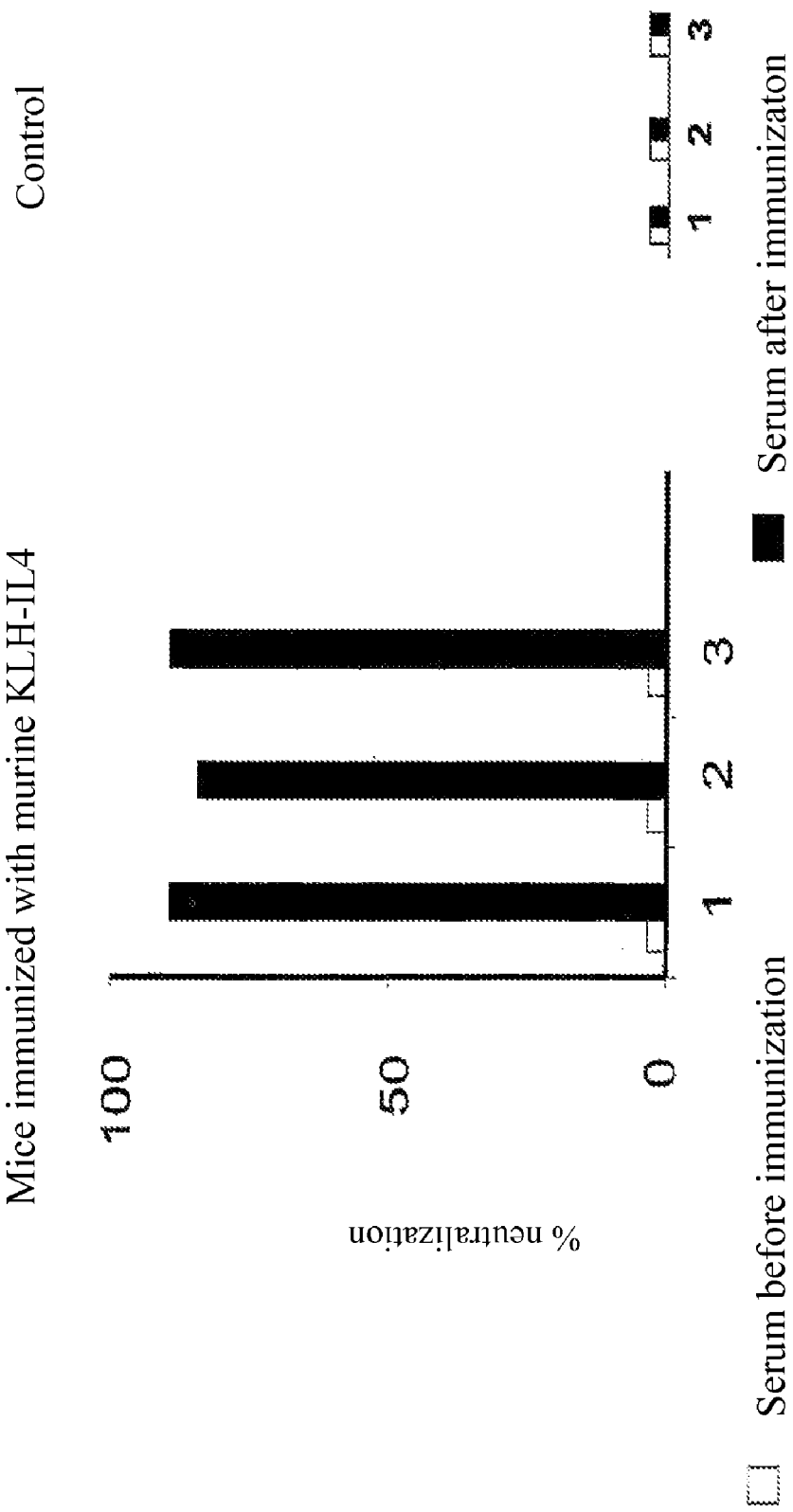
FIG. 12 illustrates the immunogenic (humoral) activity of the human KLH-IL4 immunogenic product through determination of the neutralizing power of antibodies obtained after immunization, towards the inducing activity of the proliferation of HT-2 cells by the ILA.

The neutralizing activity of such antibodies induced by the human KLH-IL4 preparation was measured by means of the biological activity test of human IL4. This test uses TF-1 cells, human cell lineage the growth of which is IL4 human-dependent (Kitamura, T. et al., 1989. J. Cell Physiol. 140:323-34). TF-1 cells are cultivated in round bottom wells of a microculture plate at a level of 10,000 cells per well. Sera diluted at 1/50 taken at D-2 and D72 preincubated for 2 hours with 50 ng/ml of human IL4 were then deposited on the TF-1 cells. The cell culture is continued at 37° C. in a humid atmosphere loaded with 5% of CO2 for 3 days. 4 hours before the end of the incubation, 0.5 µCi of titered thymidine/well were added. The neutralizing sera prevent the human IL4 from inducing the proliferation of TF-1 cells, while non neutralizing sera allow for proliferation of such cells. The results are expressed in neutralization percentage. FIG. 12 shows the obtained results.

The antibodies induced by the complex are neutralizing.

Example 28

Immunogenic Activity of the KLH-IFNα Heterocomplex

A. Material and Methods

The immunogenic (humoral) activity of the KLH-human IFNα preparation compared to that of the human IFNα was studied in 18 to 20 g balb c mouse.

1—Immunization

At days 0, 7, 14, 21, a group of 3 mice receives a 0.1 ml (10 µg) injection of an AIF emulsion through the intramuscular route. A 5 µg booster injection in AIF is given at D60.

A blood sample at the retro-orbital level is taken from each mouse before the first injection at D-2.

3 control mice receive the same preparations without an immunogen.

The mice are sacrificed 12 days after the last immunization.

2—Toxicity

The abnormal toxicity is sought in 3 mice receiving one human dosis (50 µg) according to the pharmacopeia.

The lack of immunotoxicity of the heterocomplex is evaluated in vitro by a cell proliferation test conducted on PBMCs cultivated in the presence of the complex and stimulated by PPD or toxoid tetanos.

B. Results

1—Lack of Toxicity of the Heterocomplex In Vivo and In Vitro

The mice both immunized with the KLH-human IFNα preparation and the human IFNα only do not show any clinical sign and no anatomic wound. The immunosuppression test shows that doses of 100 ng/ml to 1 µg/ml of KLH-human IFNα do not reduce the proliferation of lymphocytes.

None of the three mice immunized with 100 µg of the heterocomplex show any sign of toxicity (temperature, cutaneous disorders, systemic or regional signs) during the 7 days following the injection.

2—Humoral Response

The humoral response is measured by the presence in the serum of antibodies of the IgG type directed against the human NFNα, determined by ELISA and expressed in titer (opposite of the dilution giving an optical density higher than 0.3). The table 2 shows the resulting antibody titers.

TABLE 2

| | Titer | |
|---|---|---|
| | D-2 | D72 |
| Control mice: | | |
| Control mouse 1 | $<500^{-1}$ | $<500^{-1}$ |
| Control mouse 2 | $<500^{-1}$ | $<500^{-1}$ |
| Control mouse 3 | $<500^{-1}$ | $<500^{-1}$ |
| Mice immunized with IFNα: | | |
| mouse 4 | $<500^{-1}$ | $96,000^{-1}$ |
| mouse 5 | $<500^{-1}$ | $128,000^{-1}$ |
| mouse 6 | $<500^{-1}$ | $96,000^{-1}$ |
| Mice immunized with the KHL-IFNα complex: | | |
| mouse 7 | $<500^{-1}$ | $96,000^{-1}$ |
| mouse 8 | $<500^{-1}$ | $96,000^{-1}$ |
| mouse 9 | $<500^{-1}$ | $128,000^{-1}$ |

The mice immunized with the KHL-human IFNα preparation show antibody titers of the IgG type equivalent to those of mice immunized with the human IFNα only.

The neutralizing activity of such antibodies was measured by means of the biological activity test of the human IFNα. (Rubinstein S, J Viral, 1981, 755-8). The aim of this test for measuring the antiviral effect is to evaluate the inhibition of the MDBK cell lysis by the VSV (Vesicular Stomatitis virus) in the presence of IFN. MDBK cells are cultivated in round bottom wells of a microculture plate at a level of 350,000 cells per well. Different dilutions of sera (1/100 at 1/800) taken at D-2 and D72 were pre-incubated for 2 hours with 5 ng/ml of human IFNα then deposited on MDBK cells. After 20 hours of cell culture performed at 37° C. in a humid atmosphere loaded with 5% of CO2, the diluted sera present in the wells are removed, the cells washed, then 100 μl containing 100 LD50 (50% lethal dosis) of VSV virus are added. 18 hours after the addition of the virus the lytic effect of the virus is measured. The neutralizing sera allow the VSV to lyse cells, while non neutralizing sera prevent such a lysis. The results are expressed in neutralization percentage.

TABLE 3

| | | 1/100 | 1/200 | 1/400 | 1/800 |
|---|---|---|---|---|---|
| Mice immunized with IFNα: | | | | | |
| mouse 4 | D-2 | 0 | 0 | 0 | 0 |
| | D72 | 100 | 75 | 65 | 50 |
| mouse 5 | D-2 | 0 | 0 | 0 | 0 |
| | D72 | 100 | 67 | 60 | 55 |
| mouse 6 | D-2 | 0 | 0 | 0 | 0 |
| | D72 | 100 | 72 | 65 | 60 |
| Mice immunized with the KLH-IFNα conjugate | | | | | |
| mouse 7 | D-2 | 0 | 0 | 0 | 0 |
| | D72 | 100 | 100 | 100 | 100 |
| mouse 8 | D-2 | 0 | 0 | 0 | 0 |
| | D72 | 100 | 100 | 100 | 100 |
| mouse 9 | D-2 | 0 | 0 | 0 | 0 |
| | D72 | 100 | 100 | 100 | 100 |

The antibodies induced by the complex have a higher neutralizing power than that induced by the human IFNα. The results are expressed in neutralization percentage.

Example 29

Immunogenic Activity of the gp160-IFNα Heterocomplex

A. Material and Methods

The immunogenic (humoral) activity of the human gp160-IFNα preparation compared to that of the human IFNα was studied in 18 to 20 g balb c mouse.

1—Immunization

At days 0, 7, 14, 21, a group of 3 mice receives a 0.1 ml (10 μg) injection of an AIF emulsion through the intramuscular route. A 5 μg booster injection in AIF is given at D60.

A blood sample at the retro-orbital level is taken from each mouse before the first injection at D-2.

3 control mice receive the same preparations without an immunogen.

The mice are sacrificed 12 days after the last immunization.

2—Toxicity

The abnormal toxicity is sought in 3 mice receiving one human dosis (100 μg) according to the pharmacopeia.

The lack of immunotoxicity of the heterocomplex is evaluated in vitro by a cell proliferation test conducted on PBMCs cultivated in the presence of the complex and stimulated by PPD or toxoid tetanos.

B. Results

1—Lack of Toxicity of the Heterocomplex In Vivo and In Vitro

The mice immunized both with the gp160-human IFNα preparation and the human IFNα only, do not show any clinical sign and no anatomic wound. The immunosuppression test shows that doses of 100 ng/ml to 1 μg/ml of gp160-human IFNα do not reduce the proliferation of lymphocytes.

None of the three mice immunized with 100 μg of the heterocomplex show any sign of toxicity (temperature, cutaneous disorders, systemic or regional signs) during the 7 days following the injection.

2—Humoral Response

The humoral response is measured by the presence in the serum of antibodies of the IgG type directed against the human IFN, determined by ELISA and expressed in titer (opposite of the dilution giving an optical density higher than 0.3).

TABLE 4

| | Titer | |
|---|---|---|
| D-2 | | D72 |
| Control mice: | | |
| Control mouse 1 | $<500^{-1}$ | $<500^{-1}$ |
| Control mouse 2 | $<500^{-1}$ | $<500^{-1}$ |
| Control mouse 3 | $<500^{-1}$ | $<500^{-1}$ |
| Mice immunized with IFNα: | | |
| mouse 4 | $<500^{-1}$ | $64,000^{-1}$ |
| mouse 5 | $<500^{-1}$ | $96,000^{-1}$ |
| mouse 6 | $<500^{-1}$ | $128,000^{-1}$ |
| Mice immunized with the gp160-IFNα complex: | | |
| mouse 7 | $<500^{-1}$ | $96,000^{-1}$ |
| mouse 8 | $<500^{-1}$ | $96,000^{-1}$ |
| mouse 9 | $<500^{-1}$ | $64,000^{-1}$ |

The mice immunized with the gp 160-human IFNα preparation present IgG type antibody titers equivalent to those of mice immunized with the human IFNα only.

The neutralizing activity of such antibodies has been measured with the help of the human IFNα biological activity test described in the former example. Results are given in neutralization %.

TABLE 5

|  |  | 1/100 | 1/200 | 1/400 | 1/800 |
|---|---|---|---|---|---|
| Mice immunized with the IFNα: | | | | | |
| mouse 4 | D-2 | 0 | 0 | 0 | 0 |
|  | D72 | 100 | 80 | 70 | 53 |
| mouse 5 | D-2 | 0 | 0 | 0 | 0 |
|  | D72 | 100 | 70 | 65 | 50 |
| mouse 6 | D-2 | 0 | 0 | 0 | 0 |
|  | D72 | 100 | 65 | 60 | 57 |
| Mice immunized with the gp160-IFNα conjugate: | | | | | |
| mouse 7 | D-2 | 0 | 0 | 0 | 0 |
|  | D72 | 100 | 100 | 100 | 100 |
| mouse 8 | D-2 | 0 | 0 | 0 | 0 |
|  | D72 | 100 | 100 | 100 | 100 |
| mouse 9 | D-2 | 0 | 0 | 0 | 0 |
|  | D72 | 100 | 100 | 100 | 100 |

The antibodies induced by the complex have a higher neutralizing power than that induced by the human IFNα.

Example 30

Immunogenic Activity of the gp160-Toxoid Tat Heterocomplex

A. Material and Methods

The immunogenic (humoral and cellular) activity of the gp160-toxoid Tat preparation compared to that of the toxoid Tat was studied in 18 to 20 g balb c mouse.

1—Immunization

At days 0, 7, 14, 21, a group of 3 mice receives a 0.1 ml (10 μg) injection of an AIF emulsion through the intramuscular route. A 5 μg booster injection in AIF is given at D-2.

A blood sample at the retro-orbital level is taken from each mouse before the first injection at d-2.

3 control mice receive the same preparations without an immunogen.

The mice are sacrificed 12 days after the last immunization.

2—Toxicity

The abnormal toxicity is sought in 3 mice receiving one human dose (100 μg) according to the pharmacopeia.

The lack of immunotoxicity of the heterocomplex is evaluated in vitro by a cell proliferation test conducted on PBMCs cultivated in the presence of the complex and stimulated by PPD or toxoid tetanos.

B. Results:

1—Lack of Toxicity of the Heterocomplex In Vivo and In Vitro

The mice immunized both with the gp 160-toxoid Tat preparation and the toxoid Tat only do not show any clinical sign and no anatomic wound. The immunosuppression test shows that doses of 100 ng/ml to 1 μg/ml of gp 160-toxoid Tat do not reduce the proliferation of lymphocytes.

None of the three mice immunized with 100 μg of the heterocomplex show any sign of toxicity (temperature, cutaneous disorders, systemic or regional signs) during the 7 days following the injection.

2—Humoral Response

The humoral response is measured by the presence in the serum of antibodies of the IgG type directed against the Tat, determined by ELISA and expressed in titer (reciprocal of the dilution giving an optical density higher than 0.3). Table 6 shows the resulting antibody titers.

TABLE 6

|  | Titer | Titer |
|---|---|---|
|  | D-2 | D72 |
| Control mice: | | |
| Control mouse 1 | $<500^{-1}$ | $<500^{-1}$ |
| Control mouse 2 | $<500^{-1}$ | $<500^{-1}$ |
| Control mouse 3 | $<500^{-1}$ | $<500^{-1}$ |
| Mice immunized with toxoid Tat: | | |
| mouse 4 | $<500^{-1}$ | $48,000^{-1}$ |
| mouse 5 | $<500^{-1}$ | $64,000^{-1}$ |
| mouse 6 | $<500^{-1}$ | $48,000^{-1}$ |
| Mice immunized with gp160-toxoid Tat conjugate: | | |
| mouse 7 | $<500^{-1}$ | $64,000^{-1}$ |
| mouse 8 | $<500^{-1}$ | $128,000^{-1}$ |
| mouse 9 | $<500^{-1}$ | $64,000^{-1}$ |

The mice immunized with the gp160-toxoid Tat preparation show higher antibody titers of the anti-Tat IgG type than those of mice immunized with the toxoid Tat only.

The neutralizing activity of such antibodies was measured by means of the Cat assay. Different dilutions of sera (1/100-1/800) taken at D-2 and D72 are incubated for 2 hours with 50 ng/ml of native Tat. Such dilutions are then deposited on HeLa cells, stably infected cells with a plasmid containing LTR of the VIH-1 as the promoter of the Chloramphenicol Acetyl transferase gene (CAT). After 24 hours of culture, the cells are lyzed and the amount of CAT protein produced is measured by an ELISA test, the Cat assay (Boehringer Mannheim). Neutralizing sera prevent the Tat protein from inducing the expression of the CAT protein, while the non neutralizing sera allow for the synthesis of such CAT protein. The results are expressed in neutralization %.

TABLE 7

|  |  | 1/100 | 1/200 | 1/400 | 1/800 |
|---|---|---|---|---|---|
| Mice immunized with toxoid Tat: | | | | | |
| mouse 4 | D-2 | 0 | 0 | 0 | 0 |
|  | D72 | 60 | 50 | 25 | 20 |
| mouse 5 | D-2 | 0 | 0 | 0 | 0 |
|  | D72 | 60 | 55 | 30 | 20 |
| mouse 6 | D-2 | 0 | 0 | 0 | 0 |
|  | D72 | 65 | 50 | 30 | 30 |
| Mice immunized with gp16-toxoid Tat conjugate: | | | | | |
| mouse 7 | D-2 | 0 | 0 | 0 | 0 |
|  | D72 | 100 | 100 | 100 | 100 |
| mouse 8 | D-2 | 0 | 0 | 0 | 0 |
|  | D72 | 100 | 100 | 100 | 100 |
| mouse 9 | D-2 | 0 | 0 | 0 | 0 |
|  | D72 | 100 | 100 | 100 | 100 |

The antibodies induced by the gp160-toxoid Tax conjugate have a higher neutralizing power than that induced by the toxoid Tat 2. Production of MIP1α

The production of MIP1α in culture supernatants of splenocytes. Splenocytes of immunized mice and control mice are isolated then cultivated in round bottom wells of a micro-culture plate at a level of 100,000 cells/well in the presence of 5 Mg/ml of p24, gp160, native Tat and a mixture of 5 μg/ml gp160 and 5 μg/ml of native Tat. The supernatants are taken after 24 hours of culture and the presence of MIP1 in the supernatants is measured by means of a R&D ELISA test. The results are expressed in µg/ml.

TABLE 8

|  |  | Gp160 | native Tat | Gp160 + native Tat | P24 |
|---|---|---|---|---|---|
| Control mice: | | | | | |
| mouse 1 D72 | MIP1α | 95 | 90 | 145 | 9 |
| mouse 2 D72 | Mip1α | 100 | 90 | 136 | 7 |
| mouse 3 D72 | MIP1α | 120 | 110 | 132 | 9 |
| Mice immunized with toxoid Tat: | | | | | |
| mouse 4 D72 | MIP1α | 145 | 130 | 190 | 7 |
| mouse 5 D72 | MIP1α | 128 | 145 | 225 | 9 |
| mouse 6 D72 | MIP1α | 150 | 230 | 295 | 10 |
| Mice immunized with gp160-toxoid Tat conjugate: | | | | | |
| mouse 7 D72 | MIP1α | 875 | 736 | 1725 | 9 |
| mouse 8 D72 | MIP1αα | 945 | 905 | 1900 | 7 |
| mouse 9 D72 | MIP1α | 1025 | 795 | 1755 | 8 |

Splenocytes of mice immunized with the gp160-toxoid Tat conjugate produce more MIP1α chemiokins than cells of mice immunized by the toxoid Tat only when they are activated, in vitro, by the immunogens used during the immunization.

4. Proliferation of Splenocytes of Immunized Mice (CMI Test)

Splenocytes of immunized mice and of control mice are isolated then cultivated in round bottom wells of a microculture plate at a level of 100,000 cells/well in the presence of p24, gp160, native Tat and a mixture of gp160 and native Tat. The cell culture is continued at 37° C. in a humid atmosphere loaded with 5% of CO2 for 6 days. 18 hours before the end of the incubation, 0.5 µCi of titered thymidine/well were added. The intensity of the immune response is proportional to the proliferation index Ip.

Ip=spm (strokes per minute) for the given antigen/ control spm

TABLE 9

|  | Gp160 | native Tat | Gp160+ native Tat | P24 |
|---|---|---|---|---|
| Control mice: | | | | |
| mouse 1 D72 | 1.1 | 1.1 | 1 | 1.2 |
| mouse 2 D72 | 1 | 1.1 | 1.1 | 1.1 |
| mouse 3 D72 | 1.2 | 1 | 1 | 1.1 |
| Mice immunized with toxoid Tat: | | | | |
| mouse 4 D72 | 1.2 | 8 | 10 | 1.1 |
| mouse 5 D72 | 1 | 9 | 9 | 1.2 |
| mouse 6 | 1 | 10 | 9 | 1.2 |

TABLE 9-continued

|  | Gp160 | native Tat | Gp160+ native Tat | P24 |
|---|---|---|---|---|
| D72 | | | | |
| Mice immunized with gp160-toxoid Tat conjugate: | | | | |
| mouse 7 D72 | 9 | 11 | 8 | 1 |
| mouse 8 D72 | 10 | 9 | 7.5 | 1 |
| mouse 9 D72 | 10.5 | 9 | 8 | 1 |

Splenocytes of mice immunized with the gp160-toxoid Tat conjugate or the toxoid Tat, proliferate, when they are activated, in vitro, with the immunogens used during the immunization.

Example 31

Immunogenic Activity of the gp160-GMTat Heterocomplex

A. Material and Methods

The immunogenic (humoral and cellular) activity of the gp160-GM Tat preparation compared to that of the toxoid Tat was studied in 18 to 20 g balb c mouse.

1—Immunization

At days 0, 7, 14, 21, a group of 3 mice receives a 0.1 ml (10 µg) injection of an emulsion in AIF through the intramuscular route. A 5 µg booster injection in AIF is given at D-2.

A blood sample at the retro-orbital level is taken from each mouse before the first injection at d-2.

3 control mice receive the same preparations without an immunogen.

The mice are sacrificed 12 days after the last immunization.

2—Toxicity

The abnormal toxicity is sought in 3 mice receiving one human dosis (100 µg) according to the pharmacopeia.

The lack of immunotoxicity of the heterocomplex is evaluated in vitro by a cell proliferation test conducted on PBMCs cultivated in the presence of the complex and stimulated by PPD or toxoid tetanos.

B. Results

Lack of Toxicity of the Heterocomplex In Vivo and In Vitro

The mice immunized both with the gp160-GM Tat preparation and the toxoid Tat only, do not show any clinical sign and no anatomic wound. The immunosuppression test shows that doses of 100 ng/ml to 1 µg/ml of gp160-toxoid Tat do not reduce the proliferation of lymphocytes.

None of the three mice immunized with 100 µg of the heterocomplex show any sign of toxicity (temperature, cutaneous disorders, systemic or regional signs) during the 7 days following the injection.

2—Humoral Response

The humoral response is measured by the presence in the serum of antibodies of the IgG type directed against the Tat, determined by ELISA and expressed in titer (reciprocal of the dilution giving an optical density higher than 0.3). Table 10 shows the resulting antibody titers.

TABLE 10

| | Titer | |
|---|---|---|
| | D-2 | D72 |
| Control mice: | | |
| Control mouse 1 | $<500^{-1}$ | $<500^{-1}$ |
| Control mouse 2 | $<500^{-1}$ | $<500^{-1}$ |
| Control mouse 3 | $<500^{-1}$ | $<500^{-1}$ |
| Mice immunized with GM Tat: | | |
| mouse 4 | $<500^{-1}$ | $64,000^{-1}$ |
| mouse 5 | $<500^{-1}$ | $64,000^{-1}$ |
| mouse 6 | $<500^{-1}$ | $48,000^{-1}$ |
| Mice immunized with the gp160-GM Tat conjugate: | | |
| mouse 7 | $<500^{-1}$ | $128,000^{-1}$ |
| mouse 8 | $<500^{-1}$ | $128,000^{-1}$ |
| mouse 9 | $<500^{-1}$ | $64,000^{-1}$ |

The mice immunized with the gp160-GM Tat preparation show higher antibody titers of the anti-Tat IgG type than those of mice immunized with the GM Tat only.

Example 32

Immunogenic Activity of the KLH-Murine TNFα Heterocomplex

A. Material and Methods

The immunogenic (humoral) activity of the KLH-murine TNFα preparation compared to that of the murine TNFα was studied in 18 to 20 g balb/c mouse.

At day 0, a group of 3 mice (group A) receives a 0.1 ml injection of an AIF emulsion through the intramuscular route containing 60 μg of the KLH-TNFα complex. A booster injection of 30 μg and 15 μg in AIF is given respectively at D21 and D60. 3 control mice receive a dosis equivalent in murine TNFα according to the same protocol. (group B)

At day 0, a group of 3 mice (group C) receives a 0.1 ml injection in AIF through intramuscular route containing 60 μg of KLH-murine TNFα heterocomplex and 30 μg of the phosphorothioate oligodeoxynucleotide 5'-TCCATGACGTTC-CTGACGTT-3' (SEQ ID NO: 2) (CpG ADN: 1826). A booster injection of 30 μg and of 15 μg of the KLH-murine TNFα heterocomplex in AIF is given respectively at D21 and D60. 3 control mice receive a dosis equivalent in murine TNFα according to the same protocol (group D).

A blood sample at the retro-orbital level is taken from each mouse before the first injection at d-2.

The mice are sacrificed 12 days after the last immunization.

2—Toxicity

The abnormal toxicity is sought in 3 mice receiving one human dose (50 μs) according to the pharmacopeia.

The lack of immunotoxicity of the heterocomplex is evaluated in vitro by a cell proliferation test conducted on PBMCs cultivated in the presence of the complex and stimulated by PPD or toxoid tetanos.

B. Results

Lack of Toxicity of the Heterocomplex In Vivo and In Vitro

The mice both immunized with the murine KLH-TNFα preparation and the murine TNFα only do not show any clinical sign and no anatomic wound. The immunosuppression test shows that doses of 100 ng/ml to 1 μg/ml of KLH-murine TFNα do not reduce the proliferation of lymphocytes.

None of the three mice immunized with 50 μg of the heterocomplex with or without the DNA CPG 1826 show any sign of toxicity (temperature, cutaneous disorders, systemic or regional signs) during the 7 days following the injection.

2—Humoral Response

The humoral response is measured by the presence in the serum of antibodies of the IgG type raised against the murine TNFα, determined by ELISA and expressed in titer. The presence of antibodies of the IgA type directed against the murine TNFα in vaginal secretions was also determined by ELISA and expressed in titer. The titer represents the opposite of the dilution giving an optical density higher than 0.3. The following table shows the resulting antibody titers.

TABLE 11

| | | | Vaginal IgA | |
|---|---|---|---|---|
| | D-2 | D72 | D-2 | D72 |
| Mice immunized with KLH-murine TNFα (group A) | | | | |
| 1 | $<500^{-1}$ | $64,000^{-1}$ | $<10^{-1}$ | $20^{-1}$ |
| 2 | | $48,000^{-1}$ | | $20^{-1}$ |
| 3 | | $64,000^{-1}$ | | $40^{-1}$ |
| Mice immunized with the Murine TNFα (group B) | | | | |
| 4 | $<500^{-1}$ | $750^{-1}$ | $<10^{-1}$ | $10^{-1}$ |
| 5 | | $1,000^{-1}$ | | $20^{-1}$ |
| 6 | | $750^{-1}$ | | $10^{-1}$ |
| Mice immunized with KLH-murine TNFα in the presence of CPG (group C) | | | | |
| 7 | $<500^{-1}$ | $128,000^{-1}$ | $<10^{-1}$ | $160^{-1}$ |
| 8 | | $256,000^{-1}$ | | $80^{-1}$ |
| 9 | | $256,000^{-1}$ | | $320^{-1}$ |
| Mice immunized with murine TNFα: in the presence of CpG (group D) | | | | |
| 7 | $<500^{-1}$ | $2000^{-1}$ | $<10^{-1}$ | $20^{-1}$ |
| 8 | | $4,000^{-1}$ | | $40^{-1}$ |
| 9 | | $3,000^{-1}$ | | $40^{-1}$ |

Example 33

Immunogenic Activity of the Tat Peptide-$_h$IgE Heterocomplex

A. Material and Methods

The immunogenic (humoral) activity of the KLH-human IgE preparation compared to that of the human IgE was studied in 18 to 20 g balb c mouse.

1—Immunization

At days 0, 7, 14, 21, a group of 3 mice receives a 0.1 ml (10 μg) injection of an AIF emulsion through the intramuscular route. A 5 μg booster injection in AIF is given at D60.

A blood sample at the retro-orbital level is taken from each mouse before the first injection at D-2.

3 control mice receive the same preparations without an immunogen.

The mice are sacrificed 12 days after the last immunization.

2—Toxicity

The abnormal toxicity is sought in 3 mice receiving one human dosis (50 μg) according to the pharmacopeia.

The lack of immunotoxicity of the heterocomplex is evaluated in vitro by a cell proliferation test conducted on PBMCs cultivated in the presence of the complex and stimulated by PPD or toxoid tetanos.

B. Results

2—Lack of Toxicity of the Heterocomplex In Vivo and In Vitro

The mice both immunized with the KLH-human IgE preparation and the human IgE only, do not show any clinical sign and no anatomic wound. The immunosuppression test shows that doses of 100 ng/ml to 1 µg/ml of KLH-human IgE do not reduce the proliferation of lymphocytes.

None of the three mice immunized with 50 µg of the heterocomplex show any sign of toxicity (temperature, cutaneous disorders, systemic or regional signs) during the 7 days following the injection.

2—Humoral Response

The humoral response is measured by the presence in the serum of antibodies of the IgG type directed against the human IgE, determined by ELISA and expressed in titer (reciprocal of the dilution giving an optical density higher than 0.3). The following table shows the resulting antibody titers.

TABLE 12

| | Titer | |
|---|---|---|
| | D-2 | D72 |
| Control mice: | | |
| 1 | <500$^{-1}$ | <500$^{-1}$ |
| 2 | | |
| 3 | | |
| Mice immunized with $_h$IgE | | |
| 4 | <500$^{-1}$ | 64,000$^{-1}$ |
| 5 | | 128,000$^{-1}$ |
| 6 | | 128,000$^{-1}$ |
| Mice immunized with KLH-$_h$IgE: | | |
| 7 | <500$^{-1}$ | 256,000$^{-1}$ |
| 8 | | 128,000$^{-1}$ |
| 9 | | 256,000$^{-1}$ |

The mice immunized with the KHL-$_h$IgF preparation show antibody titers of the IgG type slightly higher than those of mice immunized with the hIgE preparation only.

Example 34

Immunogenic Activity of the KLH-Ricin-β Heterocomplex

A. Material and Methods

The immunogenic (humoral) activity of the KLH-Ricin-β preparation compared to that of the ricin β fragment was studied in 18 to 20 g balb/c mouse.

1—Immunization

At days 0, 7, 14, 21, a group of 3 mice receives a 0.1 ml (10 μg) injection of an AIF emulsion through the intramuscular route. A 5 μg booster injection in AIF is given at D60.

A blood sample at the retro-orbital level is taken from each mouse before the first injection at D-2.

3 control mice receive the same preparations without an immunogen.

The mice are sacrificed 12 days after the last immunization.

2—Toxicity

The abnormal toxicity is sought in 3 mice receiving one human dose (50 μg) according to the pharmacopeia.

The lack of immunotoxicity of the heterocomplex is evaluated in vitro by a cell proliferation test conducted on PBMCs cultivated in the presence of the complex and stimulated by PPD or toxoid tetanos.

B. Results

3—Lack of Toxicity of the Heterocomplex In Vivo and In Vitro

The mice both immunized with the human KLH-Ricin-preparation and the ricin β-fragment only do not show any clinical sign and no anatomic wound. The immunosuppression test shows that doses of 100 ng/ml to 1 μg/ml of KLH-ricin β do not reduce the proliferation of lymphocytes.

None of the three mice immunized with 50 μg of the heterocomplex show any sign of toxicity (temperature, cutaneous disorders, systemic or regional signs) during the 7 days following the injection.

2—Humoral Response

The humoral response is measured by the presence in the serum of antibodies of the IgG type directed against the β fragment of ricin, determined by ELISA and expressed in titer (reciprocal of the dilution giving an optical density higher than 0.3). The following table shows the resulting antibody titers.

TABLE 13

| | Titer | |
|---|---|---|
| | D-2 | D72 |
| Control mice: | | |
| 1 | $<500^{-1}$ | $<500^{-1}$ |
| 2 | | |
| 3 | | |
| Mice immunized with ricin-β | | |
| 4 | $<500^{-1}$ | $256{,}000^{-1}$ |
| 5 | | $512{,}000^{-1}$ |
| 6 | | $256{,}000^{-1}$ |
| Mice immunized with KLH-Ricin-β | | |
| 7 | $<500^{-1}$ | $256{,}000^{-1}$ |
| 8 | | $256{,}000^{-1}$ |
| 9 | | $128{,}000^{-1}$ |

The neutralizing activity of such antibodies was checked by the injection to the mouse of mixtures of anti-Ricin-β and ricin serum which did not cause the animal's death, contrary to what was observed during the administration to the mouse of ricin and normal serum mixtures.

REFERENCES

Adler H L, McCurdy M A, Kattan M W, Timme T L, Scardino P T, Thompson T C. Elevated levels of circulating interleukin-6 and transforming growth factor-beta 1 in patients with metastatic prostatic carcinoma. J Urol 1999; 161: 182-7

Aucouturier J et al., Adjuvants designed for veterinary and human vaccines. Vaccine 2001 19:2666-72

Baras B. et al., Single-dose mucosal immunization with biodegradable microparticles containing a *Schistosoma mansoni* antigen. Infect Immun. (1999)67:2643-8) Basak A, Boudreault A, Chen A, Chretien M, Seidah N G, Lazure C, Application of the multiple antigenic peptides (MAP) strategy to the production of prohormone convertases antibodies: synthesis, characterization and use of 8-branched immunogenic peptides: J Pept Sci 1995 November-December; 1(6):385-95

Cowan et al, Induction of TNF alpha in human neuronal cells by extracellular human T-cell lymphotropic virus Type 1 Taxi, Journal of virology, 1997, 6982-6989

Ferreira F K et al, 1993, Purification and characterization of recombinant Bet v1, the major Birch pollen allergen: immunological equivalence to natural Bet v1; J. Biol. Chem., 268: 19574.

Fouts T R, Tuskan R, Godfrey K, Reitz M, Hone D, Lewis G K, DeVico A L. Expression and characterization of a single-chain polypeptide analogue of the human immunodeficiency virus type 1 gp120-CD4 receptor complex. J. Virol. 2000 December, 74(24): 11427-36.

Fouts T. Godfrey K, Bobb K, Montefiori D, Hanson C V, Kalyanaraman V S, DeVico A, Pal R. Cross-linked HIV-1 envelop-CD4 receptor complexes elicit broadly cross-reactive neutralizing antibodies in rhesus macaques. Proc. Natl. Acad. Sci. USA 2002, Sep. 3; 99(18):11842-7. Epun 21 août 2002

Le Buanec et al., HPV-16 E7 but not E6 oncogenic protein triggers both cellular immunosuppression and angiogenic processes. Biomed Pharmacother. 1999; 53: 424-31

Morgenstern J P et al., Amino acid sequence of Feld1, the major allergen of the domestic cat: protein sequence analysis and cDNA cloning, PNAS, 1991, 88:9690

Mori N et al., Interleukine-10 gene expression in adult t-cell leukaemia, Blood, 1996, 1035-45

Sementchenko V I, Schweinfest C W, Papas T S, Watson D K., ETS2 function is required to maintain the transformed state of human prostate cancer cells. Oncogene 1998; 17:2883-8.

Tovey E R et al, Mite faeces are a major source of house dust allergens. Nature, 1981, 289:592-593.

Yoshiji H et al., Expression of vascular endothelial growth factor, its receptor, and other angiogenic factors in human breast cancer. Cancer Res 1996, 56:2013-6

Zagury D et al, Interferon alpha and Tat involvement in the immunosuppression of uninfected T cells and C—C chemokine decline in AIDS. Proc Natl Acad Sci USA 1998; 95 : 3851-6.

Zusman I, Sandler B, Gurevich P, Zusman R, Smirnoff P, Tendler Y, Bass D, Shani A, Idelevich E, Pfefferman R, Davidovich B, Huszar M, Glick J. Comparative study of the role of serum levels of p53 antigen and its tumor cell concentration in colon cancer detection. Hum. Antibodies Hybridomas. (1996)

The invention claimed is:

1. A stable immunogenic product for inducing antibodies raised against a TNFα protein in a subject, the immunogenic product comprising protein immunogenic heterocomplexes comprising TNFα protein molecules associated with KLH carrier protein molecules, more than 1% and less than 40% of the TNFα protein molecules are directly covalently linked to the KLH carrier protein molecules, and more than 60% of the TNFα protein molecules are non-covalently associated with the KLH carrier protein, wherein said stable immunogenic product is produced by a process comprising the following steps:
a) incubating TNFα proteins and KLH carrier molecules in a molar ratio TNFα:KLH ranging from 10:1 to 50:1 in the presence of glutaraldehyde to produce immunogenic heterocomplexes;
b) removing excess glutaraldehyde;
c) stabilizing the immunogenic heterocomplexes with formaldehyde;
d) adding glycine to block the reaction with formaldehyde in step c);
e) performing a dialysis of the product obtained at step d); and
f) collecting the product comprising immunogenic heterocomplexes prepared at step e).

2. An immunogenic product according to claim 1, wherein each immunogenic heterocomplex comprises a plurality of TNFα proteins covalently linked to a KLH carrier protein molecule.

3. An immunogenic product according to claim 2, wherein the plurality of TNFα proteins is a plurality of specimens of a single TNFα protein.

4. An immunogenic product according to claim 1, wherein in step a) the TNFα proteins and the KLH carrier molecules are incubated in the presence of glutaraldehyde at a final concentration between 0.002-0.03M, for 20-60 minutes.

5. The immunogenic product according to claim 4, wherein dialysis of the product in step e) occurs by means of a dialysis membrane having a 3 kDa cutoff.

SEQUENCE LISTING

```
<160> NUMBER OF SEQ ID NOS: 2

<210> SEQ ID NO 1
<211> LENGTH: 32
<212> TYPE: PRT
<213> ORGANISM: Artificial Sequence
<220> FEATURE:
<223> OTHER INFORMATION: Synthetic peptide

<400> SEQUENCE: 1

Lys Thr Ala Cys Thr Asn Cys Thr Cys Lys Lys Cys Cys Phe His Cys
1               5                   10                  15

Gln Val Cys Phe Ile Thr Lys Ala Leu Gly Ile Ser Thr Gly Arg Lys
            20                  25                  30

<210> SEQ ID NO 2
<211> LENGTH: 20
<212> TYPE: DNA
<213> ORGANISM: Artificial Sequence
<220> FEATURE:
<223> OTHER INFORMATION: Synthetic oligodeoxynucleotide

<400> SEQUENCE: 2
tccatgacgt tcctgacgtt                                                   20
```

6. The immunogenic product according to claim 4, wherein in step c) the immunogenic heterocomplexes are stabilized by adding formaldehyde to a final concentration of about 33 mM for 12 to 48 hours.

7. The immunogenic product according to claim 6, wherein in step d) the reaction is blocked by adding glycine to a final concentration of about 0.1M for about 1 hour.

8. A composition comprising an immunogenic product according to claim 1.

9. A pharmaceutical composition comprising an immunogenic product according to claim 1 in association with one or more physiologically compatible excipients.

10. An immunogenic composition comprising an immunogenic product according to claim 1 in association with one or more physiologically compatible excipients.

11. An immunogenic composition according to claim 10, comprising a CpG immunity adjuvant.

12. A vaccine composition comprising an immunogenic product according to claim 1 in association with one or more physiologically compatible excipients.

* * * * *